(12) United States Patent
Yeung

(10) Patent No.: US 7,938,818 B2
(45) Date of Patent: May 10, 2011

(54) ALLEVIATE BACK PAIN BY INCREASING PH OF THE DISC

(76) Inventor: Jeffrey E. Yeung, San Jose, CA (US)

( * ) Notice: Subject to any disclaimer, the term of this patent is extended or adjusted under 35 U.S.C. 154(b) by 761 days.

(21) Appl. No.: 11/919,806

(22) PCT Filed: May 3, 2006

(86) PCT No.: PCT/US2006/017239
§ 371 (c)(1),
(2), (4) Date: Nov. 2, 2007

(87) PCT Pub. No.: WO2006/119455
PCT Pub. Date: Nov. 9, 2006

(65) Prior Publication Data
US 2009/0082719 A1    Mar. 26, 2009

(51) Int. Cl.
*A61M 31/00* (2006.01)
*A61F 2/46* (2006.01)
(52) U.S. Cl. ............... 604/506; 604/500; 606/86 R

(58) Field of Classification Search ............ 606/86 R, 606/92–94; 604/500, 506
See application file for complete search history.

(56) References Cited

U.S. PATENT DOCUMENTS

| | | | |
|---|---|---|---|
| 2002/0173851 A1* | 11/2002 | McKay | 623/17.11 |
| 2004/0092933 A1* | 5/2004 | Shaolian et al. | 606/61 |
| 2006/0200245 A1* | 9/2006 | Trieu | 623/17.16 |

* cited by examiner

*Primary Examiner* — Kevin C Sirmons
*Assistant Examiner* — Catherine N Witczak
(74) *Attorney, Agent, or Firm* — Carol Titus; GSS Law Group

(57) ABSTRACT

The intervertebral disc is avascular. With aging, calcified layers occlude the capillaries at the cartilaginous endplates, reducing diffusion of nutrients and oxygen from capillaries into the avascular disc. Under anaerobic condition, excessive production of lactic acid decreases intradiscal pH and irritates surrounding nerves, causing persistent back pain. Antacid is injected into the painful disc to increase pH and alleviate back pain.

17 Claims, 24 Drawing Sheets

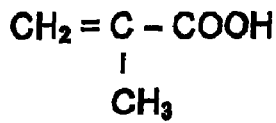
Figure 30
Methacrylic acid or
methyl-methacrylic acid
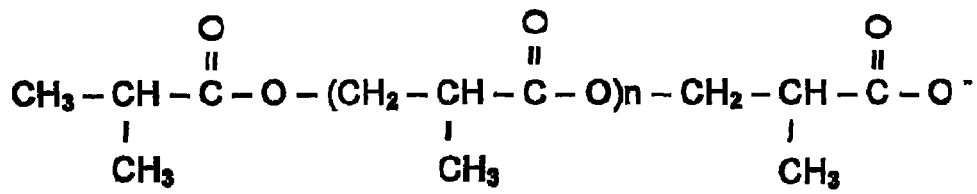
Poly-methyl-methacrylate (PMMA)
Figure 31
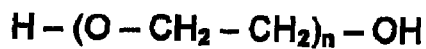
Figure 32
Polyethylene glycol (PEG)
Figure 33
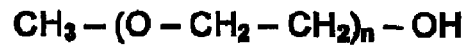
Methoxy PEG
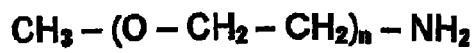
Figure 34
Methoxy PEG amine
Figure 35
PEG di-amine

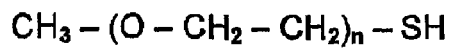
CH₃ – (O – CH₂ – CH₂)ₙ – SH
Figure 36
Methoxy sulf-hydro – PEG
Figure 37
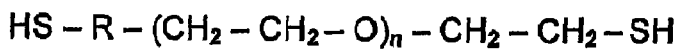
HS – R – (CH₂ – CH₂ – O)ₙ – CH₂ – CH₂ – SH
Di-sulf-hydro – PEG (Di-SH-PEG)
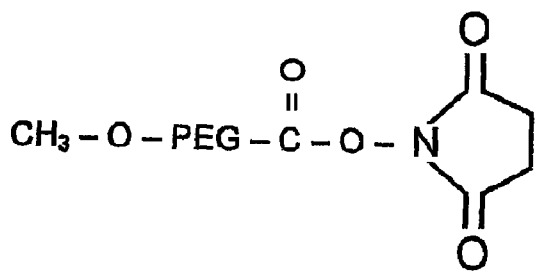
Figure 38
Methoxy-PEG-N-Hydroxysuccinimide
(Methoxy-PEG-NHS)
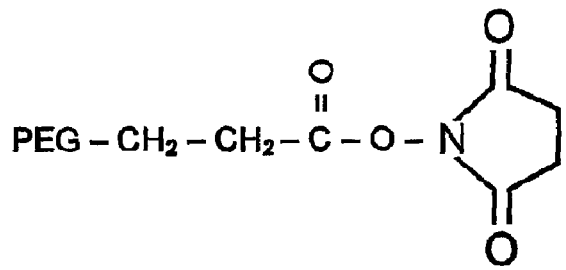
Figure 39
PEG-propionate-N-hydroxysuccinimide
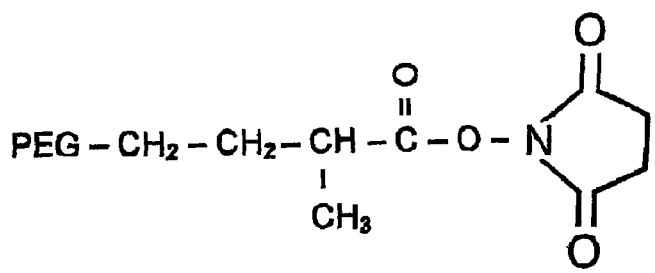
Figure 40
PEG-butanoate-N-hydroxysuccinimide

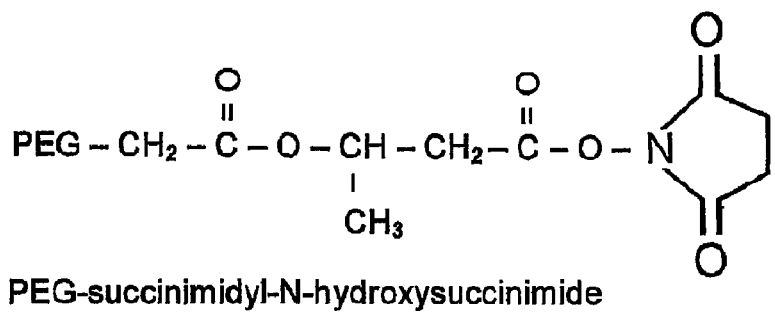
Figure 41
PEG-succinimidyl-N-hydroxysuccinimide
Figure 42
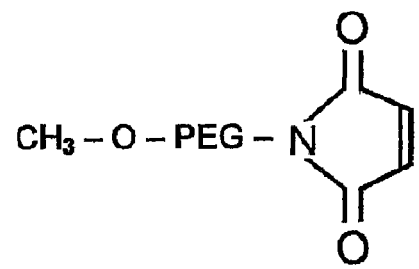
Methoxy-PEG-maleimide
(Methoxy-PEG-MAL)
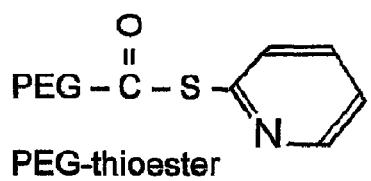
PEG-thioester
Figure 43
Figure 44
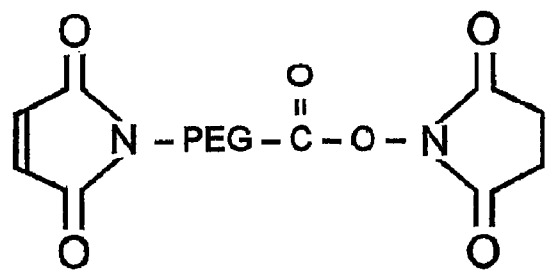
Maleimide-PEG-N-hydroxysuccinimide
(MAL-PEG-NHS)
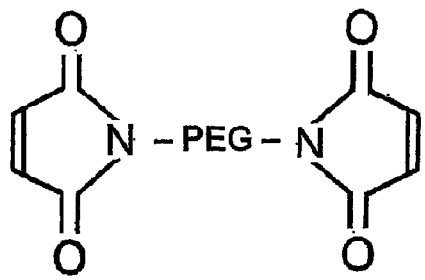
Figure 45
Maleimide-PEG-maleimide
(MAL-PEG-MAL)

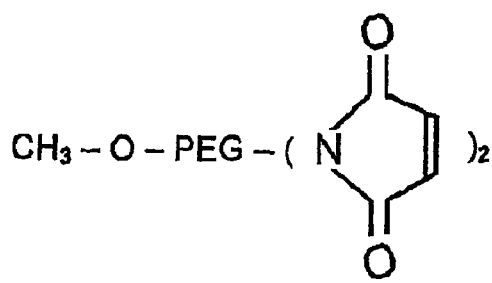
Figure 46
Methoxy-PEG-di-maleimide
(Methoxy-PEG-di-MAL)
Figure 47
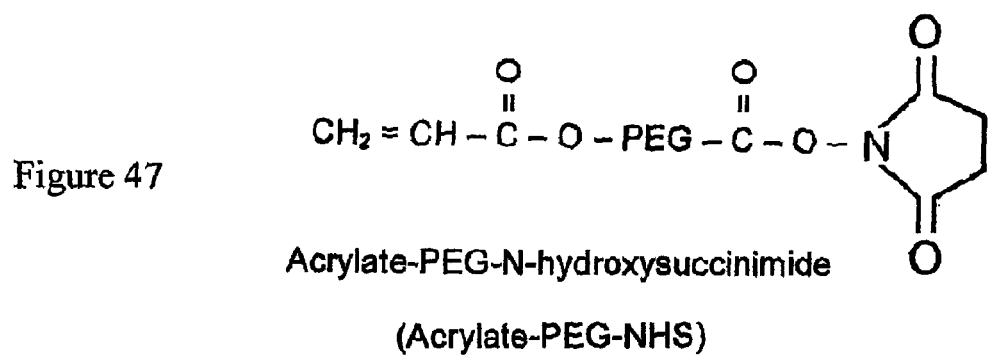
Acrylate-PEG-N-hydroxysuccinimide
(Acrylate-PEG-NHS)
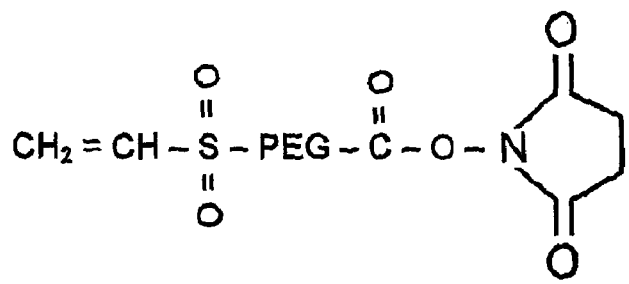
Figure 48
Vinyl sulfone-PEG-N-hydroxysuccinimide Di- N-hydroxy-succinimide -PEG

+

HS – PEG – SH
HS – PEG – SH
Di-sulf-hydro-PEG

Crosslinking Reaction  2

N-hydroxysuccinimide

Crosslinking Reaction

Polymer

Maleimide-PEG-N-hydroxysuccinimide

+

Di-sulf-hydro-PEG
HS – PEG – SH
HS – PEG – SH

Crosslinking Reaction

N-hydroxysuccinimide

Crosslinking Reaction

Polymer

Di-maleimide-PEG

+

HS – PEG – SH
HS – PEG – SH

Di-sulf-hydro-PEG

Polymer

Di-thioester-PEG

+

Di-amine-PEG      $H_2N - PEG - NH_2$

Di-sulf-hydro-PEG   $HS - PEG - SH$

Polymer

ALLEVIATE BACK PAIN BY INCREASING PH OF THE DISC

FIELD OF INVENTION

This invention relates to methods for increasing pH within an intervertebral disc by injecting antacid to neutralize lactic acid, thereby reducing acid irritation and back pain.

BACKGROUND

Low back pain is a leading cause of disability and lost productivity. Up to 90% of adults experience back pain at some time during their lives. Back pain is second only to upper respiratory infections in frequency of physician visits. In the United States, the economic impact of this malady has been reported to range from $50-$100 billion each year, disabling 5.2 million people. Though the sources of low back pain are varied, the intervertebral disc is thought to play a central role in most cases. Degeneration of the disc initiates pain in other tissues by altering spinal mechanics and producing non-physiologic stress in surrounding tissues.

A healthy intervertebral disc absorbs most of the compressive load of the spine. The facet joints 129 of the vertebral bodies 159 share only about 16% of the load. The disc 100 consists of three distinct parts: the nucleus pulposus 128, the annular layers 378 and the cartilaginous endplates 105, as shown in FIG. 1. The disc maintains its structural properties largely through its ability to attract and retain water. A normal disc 100 contains 80% water in the nucleus pulposus 128. The nucleus pulposus 128 within a normal disc 100 is rich in water absorbing sulfated glycosaminoglycans, creating the swelling pressure to provide tensile stress within the collagen fibers of the annulus 378, as shown in FIG. 2. The swelling pressure produced by high water content is crucial to supporting the annular layers 378 for sustaining compressive loads.

In adults, the intervertebral disc is avascular. Survival of the disc cells depends on diffusion of nutrients from blood vessels 112 and capillaries 107 within the vertebral bodies 159 through the cartilage 106 of the endplates 105, as shown in FIG. 2. Diffusion of nutrients also permeates from peripheral blood vessels adjacent to the outer annulus 378, but these nutrients can only permeate up to 1 cm into the annular layers 378 of the disc. An adult disc can be as large as 5 cm in diameter; hence diffusion through the cranial and caudal endplates 105 is crucial for maintaining the health of the nucleus pulposus 128 and inner annular layers 378 of the disc 100.

Calcium pyrophosphate and hydroxyapatite are commonly found in the endplate 105 and nucleus pulpous 128. Beginning as young as 18 years of age, calcified layers begin to accumulate in the cartilaginous endplate 105. The blood vessels 112 and capillaries 107 at the bone-cartilage 106 interface gradually occlude due to the build-up of calcified layers 108 which form into bone, as shown in FIG. 3. Bone formation at the endplate 105 increases with age.

When the endplate 105 is obliterated by bone, diffusion of nutrients and oxygen through the calcified 108 endplate 105 into the avascular disc 100 is greatly diminished. Oxygen concentration in the central part of the nucleus is extremely low. Cellularity of the disc is already low compared to most tissues. To obtain necessary nutrients and oxygen, cell activity is restricted to being at or in very close proximity to the cartilaginous endplate 105. Furthermore, oxygen concentrations are very sensitive to changes in cell density or consumption rate per cell.

The supply of sulfate into the nucleus pulposus 128 for biosynthesizing sulfated glycosaminoglycans is also restricted by the calcified 108 endplates 105. As a result, the sulfated glycosaminoglycan concentration decreases, leading to lower water content and swelling pressure within the nucleus pulposus 128. During normal daily compressive loading on the spine, the reduced pressure within the nucleus pulposus 128 can no longer distribute the forces evenly along the circumference of the inner annulus 378 to keep the lamellae bulging outward. As a result, the inner lamellae sag inward, while the outer annulus 378 continues to bulge outward, causing delamination 114 of the annular layers 378, as shown in FIG. 3.

The shear stresses causing annular delamination 114 and bulging are highest at the posteriolateral portions adjacent to the neuroforamen 121. The nerve 194 is confined within the neuroforamen 121 between the disc and the facet joint 129. Hence, the nerve 194 at the neuroforamen is vulnerable to impingement by the bulging disc 100 or bone spurs, as shown in FIG. 4.

When oxygen concentration in the disc falls below 0.25 kPa (1.9 mm Hg), production of lactic acid dramatically increases with increasing distance from the endplate. The pH within the disc falls as lactic acid concentration increases. Lactic acid diffuses through micro-tears of the annulus irritating the richly innervated posterior longitudinal ligament 195, facet joint 129 and/or nerve root 194, FIG. 4. Studies indicate that lumbar pain correlates well with high lactate levels and low pH (Diamant B., Karlsson J., Nachemson A.: Correlation between lactate levels and pH in discs of patients with lumbar rhizopathies, Experientia, Dec 15:24(12), 1195-1196, 1968). The mean pH of symptomatic discs was significantly lower than the mean pH of the normal discs (Kitano T., Zerwekh J E, Usui Y., Edwards M L, Flicker P L, Mooney V.: Biochemical changes associated with the symptomatic human intervertebral disk, Clinical Orthopedic Related Research, August (293), 372-377, 1993). The acid concentration is three times higher in symptomatic discs than normal discs. In symptomatic discs with pH 6.65, the acid concentration within the disc is 5.6 times the plasma level. In some preoperative symptomatic discs, nerve roots were found to be surrounded by dense fibrous scars and adhesions with remarkably low pH 5.7-6.30 (Nachemson A: Intradiscal measurements of pH in patients with lumbar rhizopathies, Acta Orthop. Scand. 40(1), 23-42, 1969). The acid concentration within the disc was as high as 50 times the plasma level.

Approximately 85% of patients with low back pain cannot be given a precise pathoanatomical diagnosis. Many of these patients are generally classified having "non-specific pain". Back pain and sciatica can be recapitulated by maneuvers that do not affect the nerve root, such as intradiscal saline injection, discography, and compression of the posterior longitudinal ligaments. It is possible that some non-specific pain is caused by lactic acid irritation secreted from the disc. Injection into the disc can flush out the lactic acid. Maneuvering and compression can also drive out the irritating acid to produce non-specific pain. Currently, no intervention other than discectomy can halt the production of lactic acid.

The nucleus pulposus is thought to function as "the air in a tire" to pressurize the disc. To support the load, the pressure effectively distributes the forces evenly along the circumference of the inner annulus 378 and keeps the lamellae bulging outward. The process of disc 100 degeneration begins with calcification 108 of the endplates 105, which hinders diffusion of sulfate and oxygen into the nucleus pulposus 128. As a result, production of the water absorbing sulfated glycosaminoglycans is significantly reduced, and the water content within the nucleus decreases. The inner annular lamellae 378 begin to sag inward, and the tension on collagen fibers within the annulus 378 is lost, as shown in FIG. 3. The degenerated disc exhibits unstable movement, similar to a flat tire. Approximately 20-30% of low-back-pain patients have been diagnosed as having spinal segmental instability. The pain may originate from stress and increased load on the facet joints 129 and/or surrounding ligaments.

Sulfate is an essential ingredient for biosynthesizing the sulfated glycosaminoglycans responsible for retaining water within the intervertebral disc 100. The rate of sulfate incorporation into the disc 100 is pH sensitive (Ohshima H., Urban J P: The effect of lactate and pH on proteoglycan and protein synthesis rates in the intervertebral disc, Spine, September: 17(9), 1079-1082, 1992). The maximum rate of sulfate incorporation occurs at pH 7.2-6.9. Below pH 6.8, the rate falls steeply. At pH 6.3, the sulfate incorporation rate is only around 32-40% of the rate at pH 72-6.9, Thus, high lactic concentration can (1) slow down the rate of sulfate incorporation to decrease production of the water-retaining sulfated glycosaminoglycans, (2) reduce the swelling pressure or water content within the disc 100, (3) decrease the capability to sustain compressive loads, and (4) irritate nerve to cause pain.

Glucosamine, chondroitin sulfate and dextrose are known to induce proteoglycan biosynthesis and were injected into the discs of patients with chronic low back pain. Fifty-seven percent of the patients showed significant improvement. The patients who showed no improvement were the ones had failed spinal surgery or had spinal stenosis and long-term disability (Klein R G, Eek B C, O'Neill C W, Elin C., Mooney V., Derby R R: Biochemical injection treatment for discogenic low back pain: a pilot study, Spine J., May-June 3(3), 220-226, 2003). Since the anaerobic production of lactic acid may cause acid irritation, buffering agent or antacid should be included in the injection. Other limited disc building ingredients, such as sodium sulfate, proline and amino acids, should also be incorporated in the injection to build sulfated glycosaminoglycans and swelling pressure within the disc.

Currently, traditional needle can easily inject into the L3-4 disc or above. The highly problematic L5-S1, L4-L5 discs are shielded between the ilia. Even with highly skillful needle manipulation, needle penetration into L5-S1 or L4-L5 disc is shallow, but the serious nutritional deprivation is within the center of the degenerated disc. In this invention, a rigid needle enters through the pedicle into the vertebral body. Then an elastically curved needle is deployed from the rigid needle to puncture through the calcified endplate into the center of the disc for injection.

Resilient straightening of a super elastically curved needle within a rigid needle is described in prior art DE 44 40 346 A1 by Andres Melzer filed on Nov. 14, 1994 and FR 2 586 183-A1 by Olivier Troisier filed on Aug. 19, 1985. The curved needles of this prior art are used to deliver liquid into soft tissue. In order to reach the intervertebral disc, the lengths of the curved and rigid needles must be at least six inches (15.2 cm). There are multiple problems when attempting to puncture the calcified endplate as described in the prior art. Shape memory material for making the curved needle usually is elastic. Nickel-titanium alloy has Young's modulus of approximately 83 GPa (austenite), 28-41 GPa (martensite). Even if the handles of both the curved 101 and rigid 220 needles are restricted from twisting, the long and elastically curved needle 101 is likely to twist within the lengthy rigid needle 220 during endplate 105 puncturing, as shown in FIGS. 11 and 12. As a result, direction of puncture is likely to be deflected and endplate puncture would fail.

Furthermore, in the prior art DE 44 40 346 A1 by Andres Melzer filed on Nov. 14, 1994 and FR 2 586 183-A1 by Olivier Troisier filed on Aug. 19, 1985, the sharp tips of their rigid needles are on the concave sides of the curved needles, as shown in FIG. 15. When puncturing a hard tissue, such as calcified endplates 105, the convex sides of the prior art curved needles 101 are unsupported and vulnerable to bending, resulting in failure to puncture through the calcified endplates 105, as shown in FIG. 15. To minimize bending or twisting, the sizes of their curved and rigid needles are required to be large. By increasing the sizes of the curved and rigid needles, friction between the curved and rigid needles greatly increases, making deployment and retrieval of the curved needle very difficult. In addition, a large opening created at the endplate 105 by the large curved needle may cause Schmorl's nodes, leakage of nucleus pulpous into the vertebral body.

This invention contains relevant supports enabling a thin elastically curved needle to puncture the calcified endplate 105 and inject into the disc. Furthermore, the non-round cross-sections of the curved needle 101 and rigid needle 220 are also relevant to prevent curved needle 101 twisting for successful puncturing through the calcified endplate 105 before injecting into the degenerated disc 100.

SUMMARY OF INVENTION

The intervertebral disc is avascular. With aging, calcified layers occlude the capillaries at the cartilaginous endplates, reducing diffusion of nutrients and oxygen from capillaries into the avascular disc. Under anaerobic condition, excessive production of lactic acid decreases intradiscal pH and irritates surrounding nerves, causing persistent back pain. Antacid is injected into the painful disc to increase pH and alleviate back pain.

In addition, addition, the normalized pH enhances transport of sodium sulfate into the disc to promote biosynthesis of sulfated glycosaminoglycans for retaining additional water to sustain compressive loads upon the disc. As a result, excessive loading and strain on the facet joints are minimized; pain is alleviated.

REFERENCE NUMBER

100 Intervertebral disc
101 Needle
102 Bevel or tapering
105 Endplate
106 Cartilage
107 Capillaries
108 Calcified layers
112 Blood vessels
114 Annular delamination
115 Epiphysis
116 Penetration marker
121 Neuroforamen
123 Spinal cord
128 Nucleus pulposus
129 Facet joint
142 Superior articular process
143 Inferior articular process
159 Vertebral body
194 Nerve root
195 Posterior longitudinal ligament
121 Neuroforamen
220 Rigid sleeve or needle
224 Puncture
230 Dilator
268 Lumen of rigid sleeve 269 Lumen of rigid needle
270 Window of rigid sleeve
271 Shape memory extension
272 Ramp in lumen of rigid needle
276 Syringe
278 Pedicle
288 Buffering agent, antacid or base
289 Filler for intervertebral disc
292 Endplate plug
374 Lumen of endplate plug
375 Static mixer
376 Second Filler for disc
377 Connector
378 Annulus

DESCRIPTION OF THE DRAWINGS

FIG. 30 shows the molecular structure of methacrylic acid, a mono component of bone cement, as a filler 289 within the syringe 276 of the curved needle 101.

FIG. 31 shows the molecular structure of the polymerized bone cement, poly-methyl-methacrylate (PMMA), a filler 289 supporting the degenerated disc 100.

FIG. 32 shows a chemical structure of polyethylene glycol, PEG, a filler 289.

FIG. 33 shows a chemical structure of methoxy-PEG, a filler 289.

FIG. 34 shows a chemical structure of methoxy-PEG-amine functional group, a filler 289.

FIG. 35 shows a chemical structure of di-amine functional groups of the PEG, a filler 289.

FIG. 36 shows a chemical structure of methoxy-PEG with a sulfhydro-functional group, a filler 289.

FIG. 37 shows a chemical structure of PEG with di-sulfhydro-functional groups, a filler 289.

FIG. 38 shows a chemical structure of N-hydroxysuccinimide, NHS, functional group on a methoxy-PEG, a filler 289.

FIG. 39 shows a chemical structure of propionate-NHS, functional group on PEG, a filler 289.

FIG. 40 shows a chemical structure of butanoate-NHS functional group on PEG, a filler 289.

FIG. 41 shows a chemical structure of succinimidyl-NHS functional group on PEG, a filler 289.

FIG. 42 shows a chemical structure of maleimide, MAL, functional group on methoxy-PEG, a filler 289.

FIG. 43 shows a chemical structure of a thio-leaving group on PEG, a filler 289.

FIG. 44 shows a chemical structure of MAL and NHS functional groups on PEG, a filler 289.

FIG. 45 shows a chemical structure of di-MAL functional groups on PEG, a filler 289.

FIG. 46 shows a chemical structure of di-MAL functional groups on methoxy-PEG, a filler 289.

FIG. 47 shows a chemical structure of acrylate and NHS functional groups on PEG, a filler 289.

FIG. 48 shows a chemical structure of vinyl sulfone and NHS functional groups on PEG, a filler 289.

DETAILED DESCRIPTION OF THE EMBODIMENTS

Figure 1:
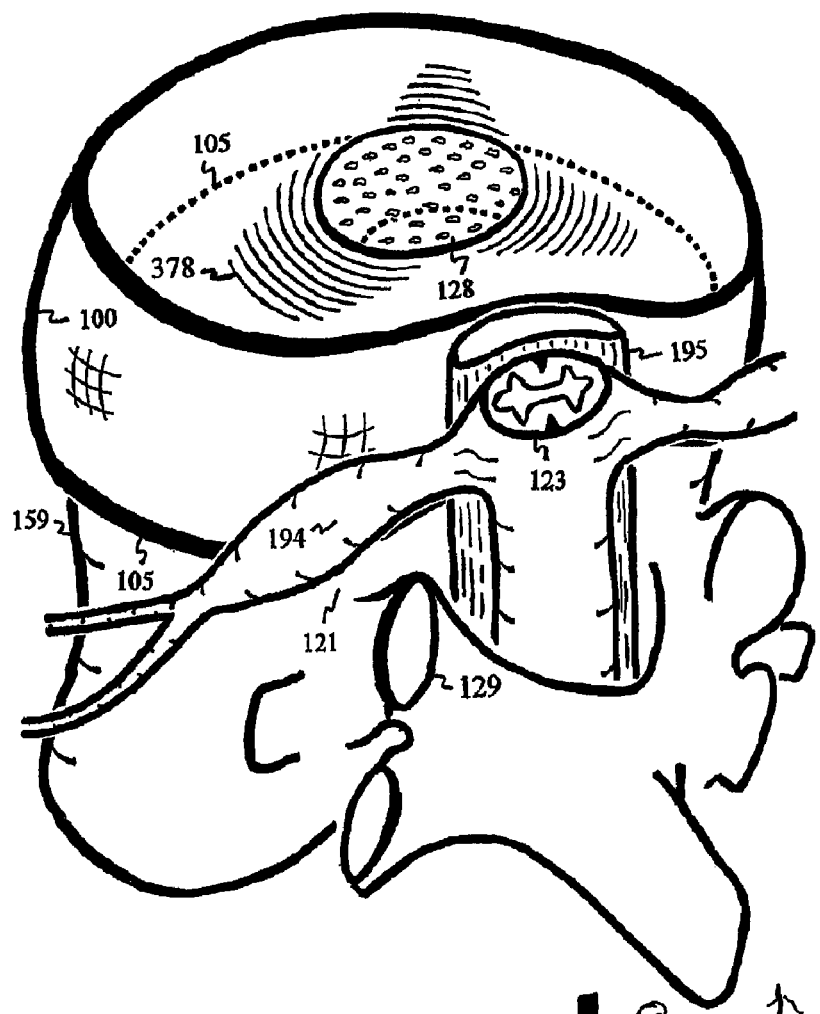
FIG. 1 depicts a healthy disc 100 with normal swelling pressure within the nucleus pulposus 128 to support the layers of annulus 378 during compressive loading.
Figure 2:
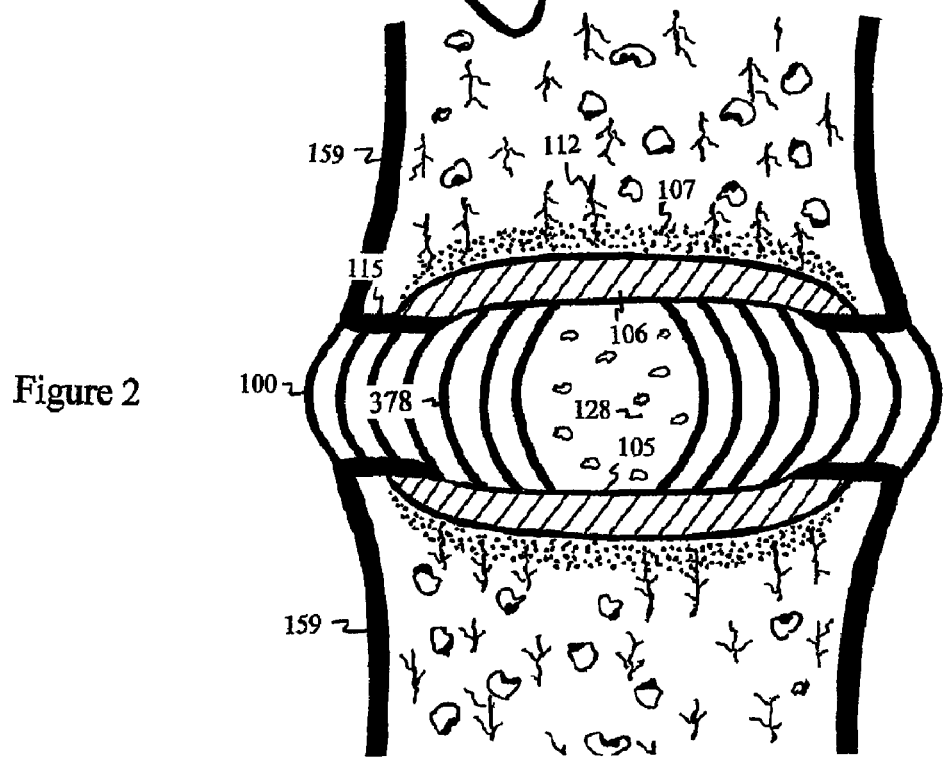
FIG. 2 shows a longitudinal view of a spine segment, displaying outward bulging of annulus 378 during compression of the disc 100 between cartilaginous 106 endplates 105.
Figure 3:
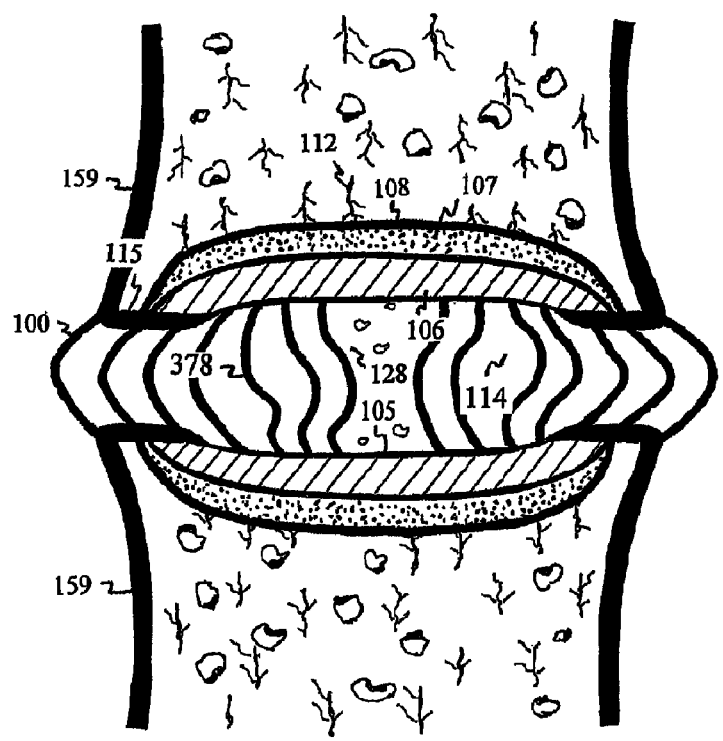
FIG. 3 shows the calcified layers 108 at the endplates 105, hindering diffusion of nutrients and oxygen from the vertebral bodies 159 into disc 100, leading to disc pressure loss and annular delamination 114.
Figure 4:
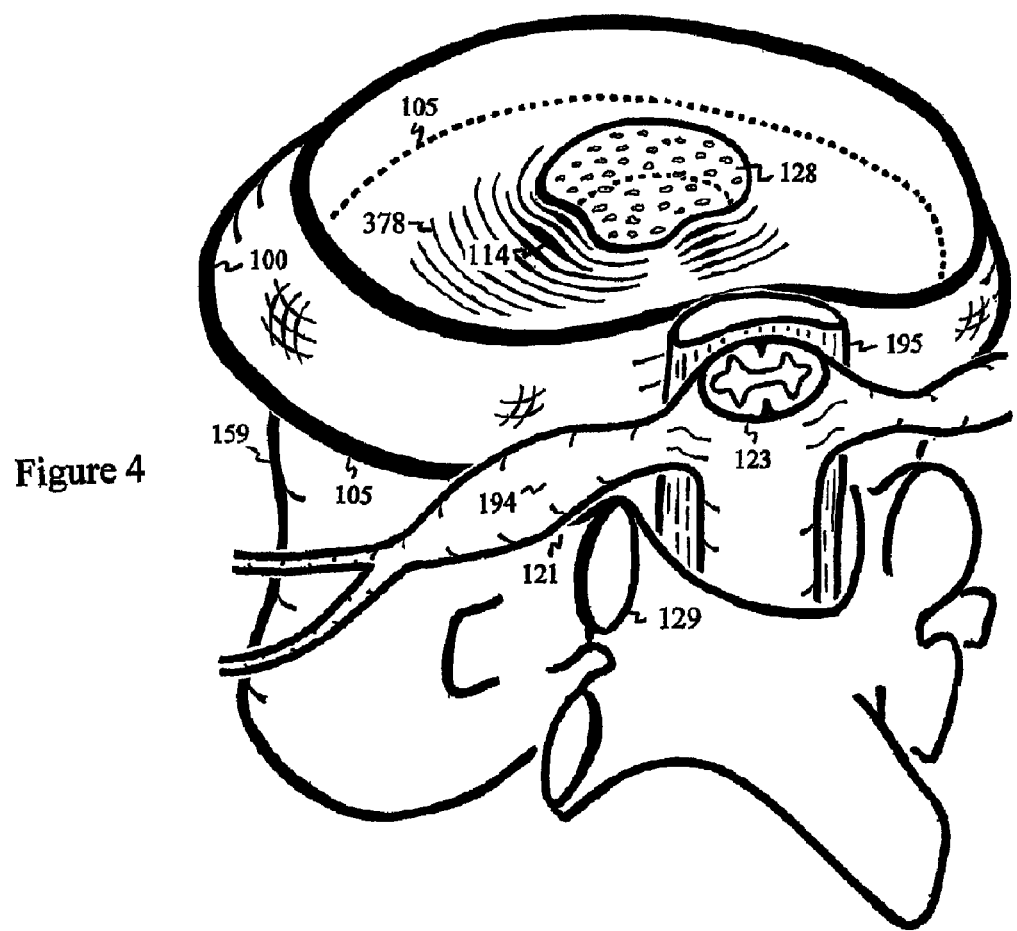
FIG. 4 depicts a degenerated and flattened disc with reduced swelling pressure within the nucleus pulposus 128 and annular delamination 114.
Figure 5:
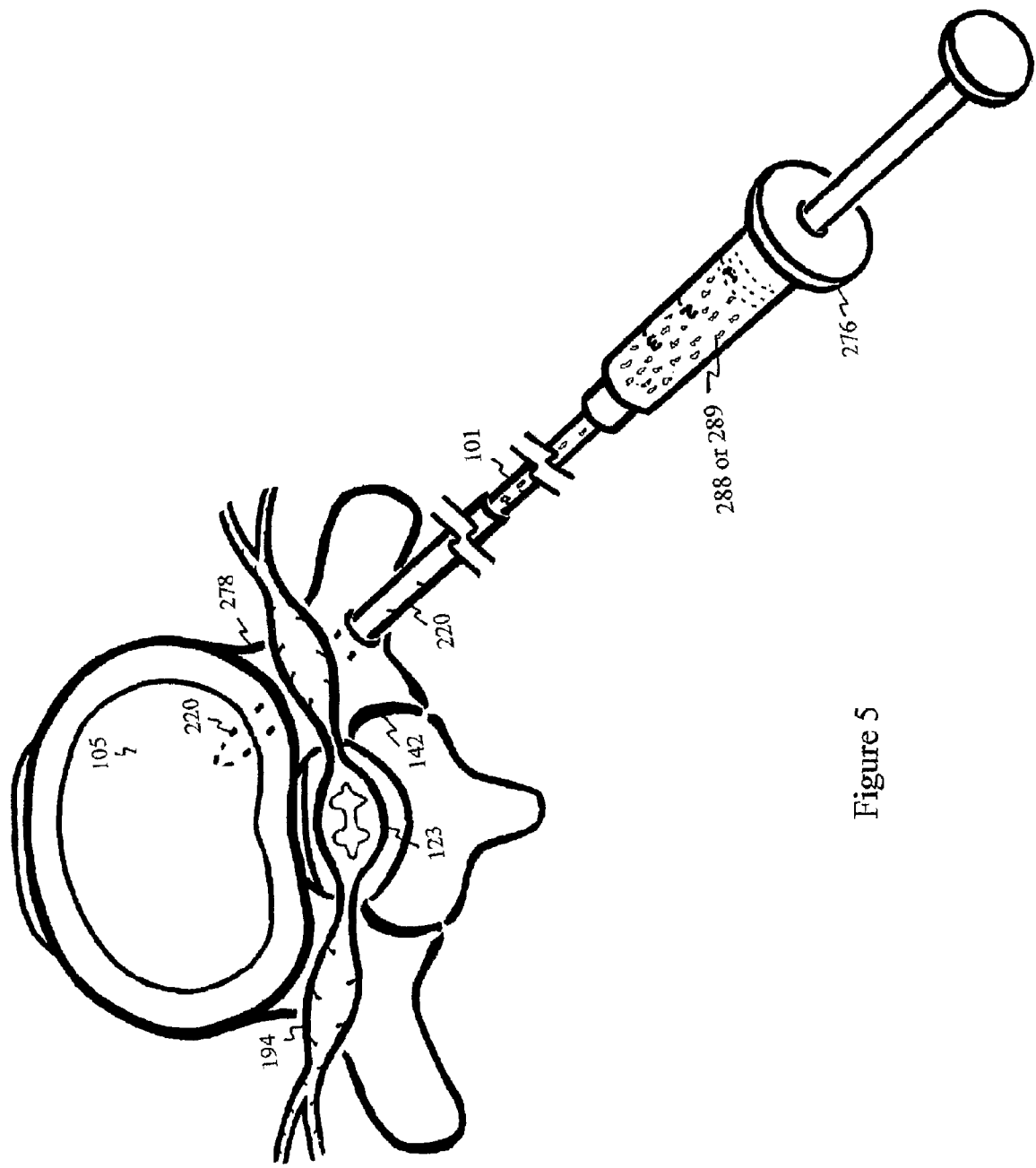
FIG. 5 depicts a syringe 276 filled with buffering agent 288 or filler 289, connected to an elastically curved needle 101 resiliently straightened within a rigid needle 220 puncturing into the pedicle 278.

FIG. 5 shows rigid needle 220 with a syringe 276 puncturing or entering the pedicle 278 adjacent to a degenerated disc 100. Pedicle puncturing may require the guidance of fluoroscopy, ultrasound, MRI or other. In addition, trocar puncturing and/or pedicle drilling is preferred prior to rigid needle 220 puncturing. Radiopaque or echogenic coating on the rigid needle 220 and curved needle 101 enhances visual detection and ascertains device position within the vertebral body 159 during endplate 105 puncturing.

Figure 6:
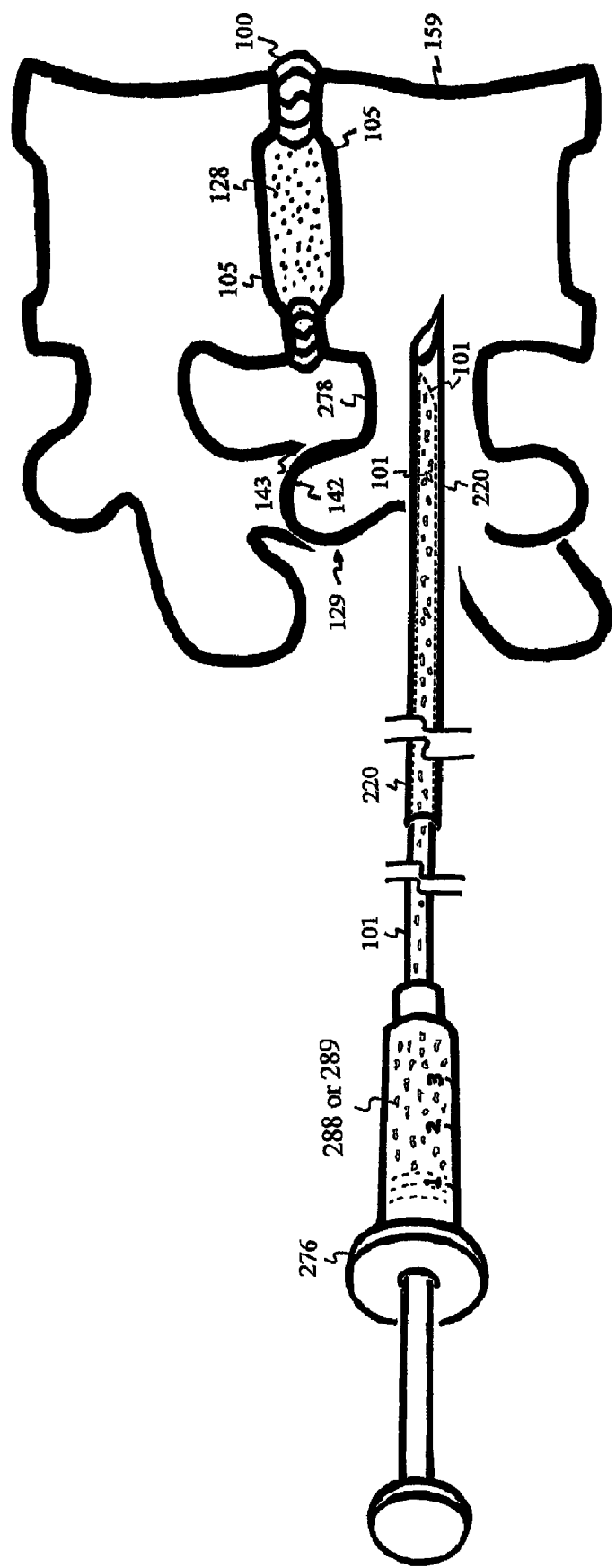
FIG. 6 shows insertion of the rigid needle 220 and elastically curved needle 101 into the pedicle 278.
Figure 7:
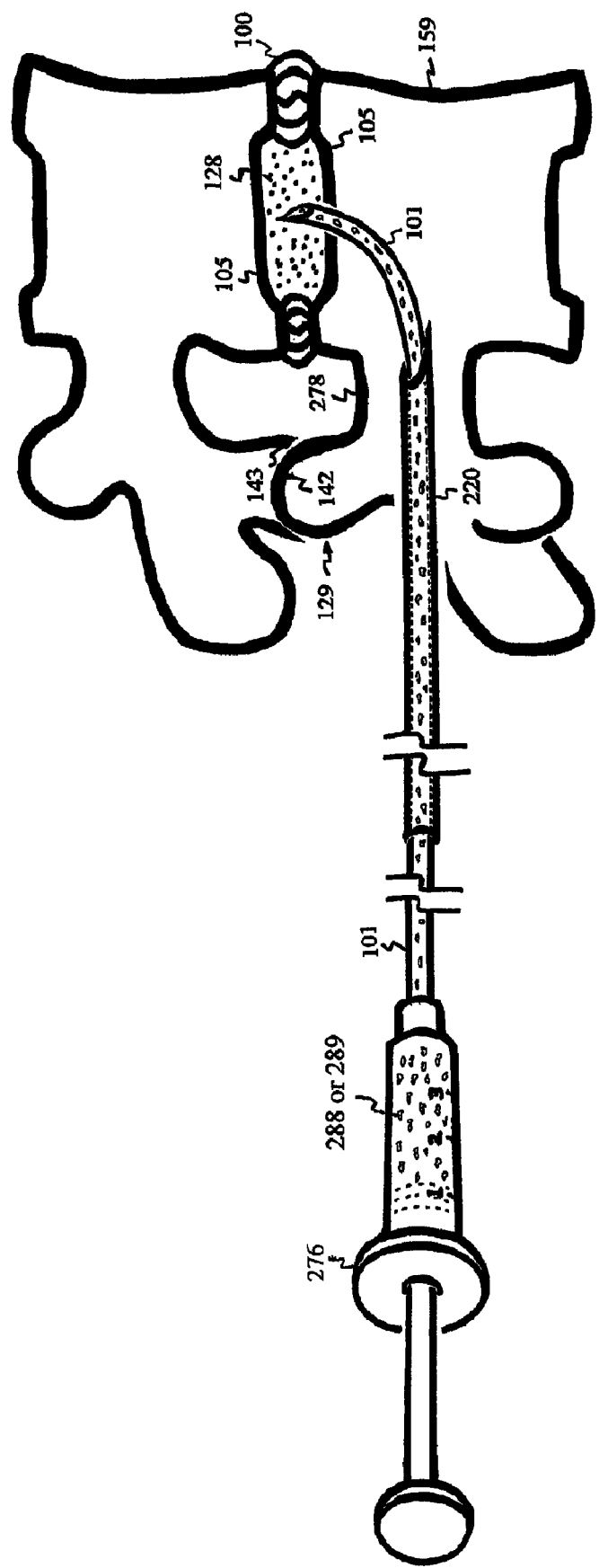
FIG. 7 depicts deployment of the elastic needle 101 from the rigid needle 220, resuming the curvature and puncturing through the calcified endplate 105 into the disc 100.
Figure 8:
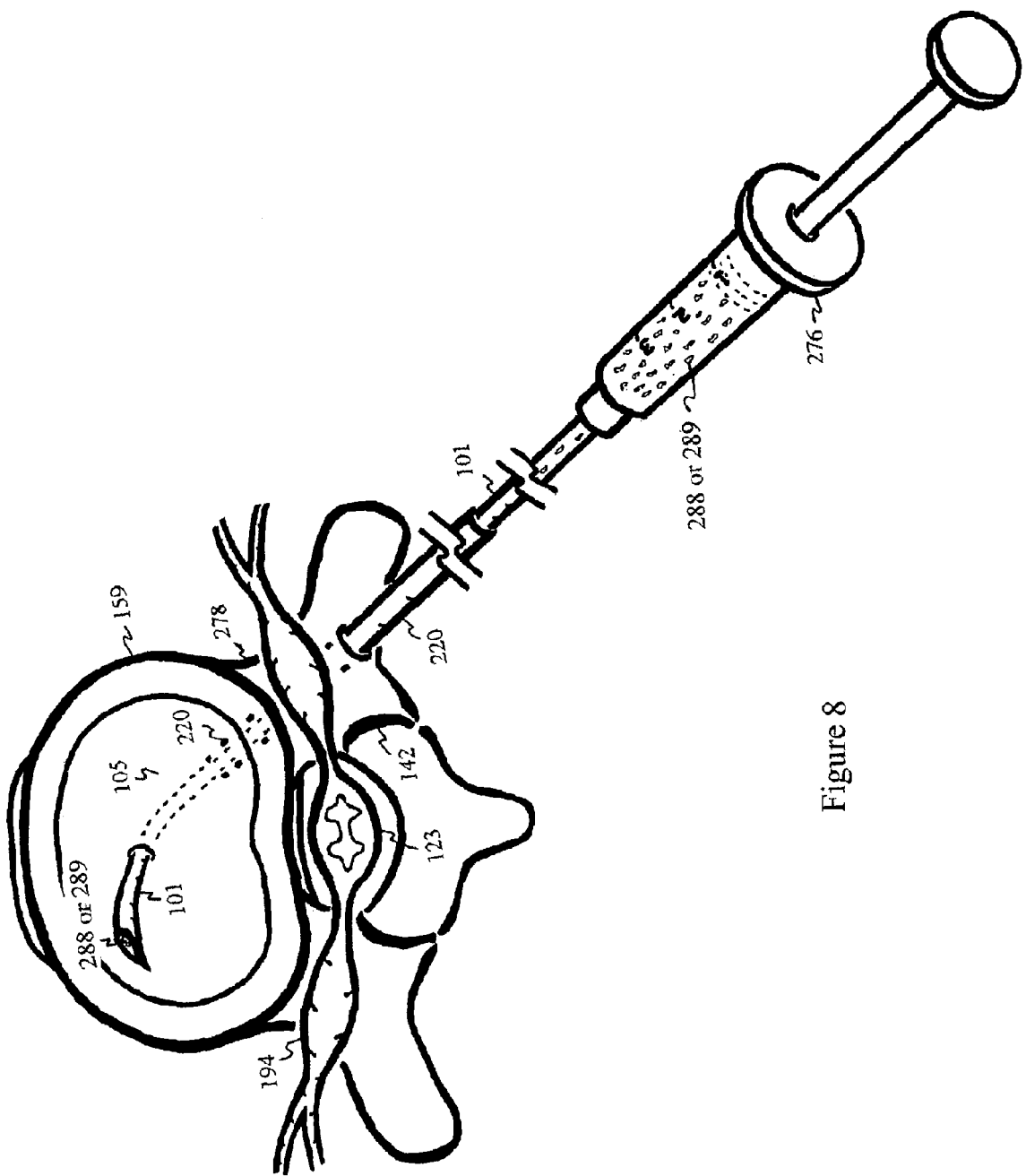
FIG. 8 depicts the top view of endplate 105 puncturing using the elastically curved needle 101 into the disc 100, not shown.
Figure 9:
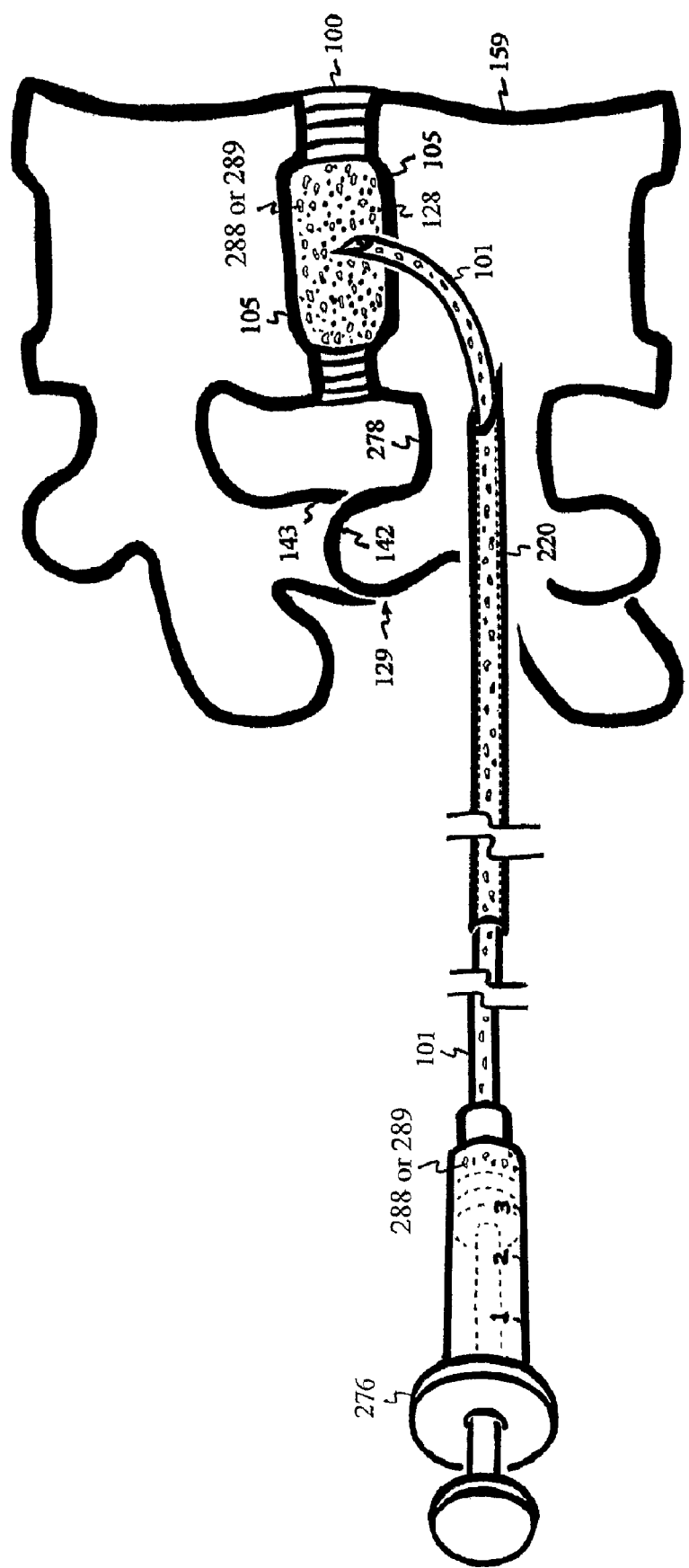
FIG. 9 depicts injection of buffering agent 288 or filler 289 from syringe 276 into the disc 100 through the elastically curved needle 100.
Figure 10:
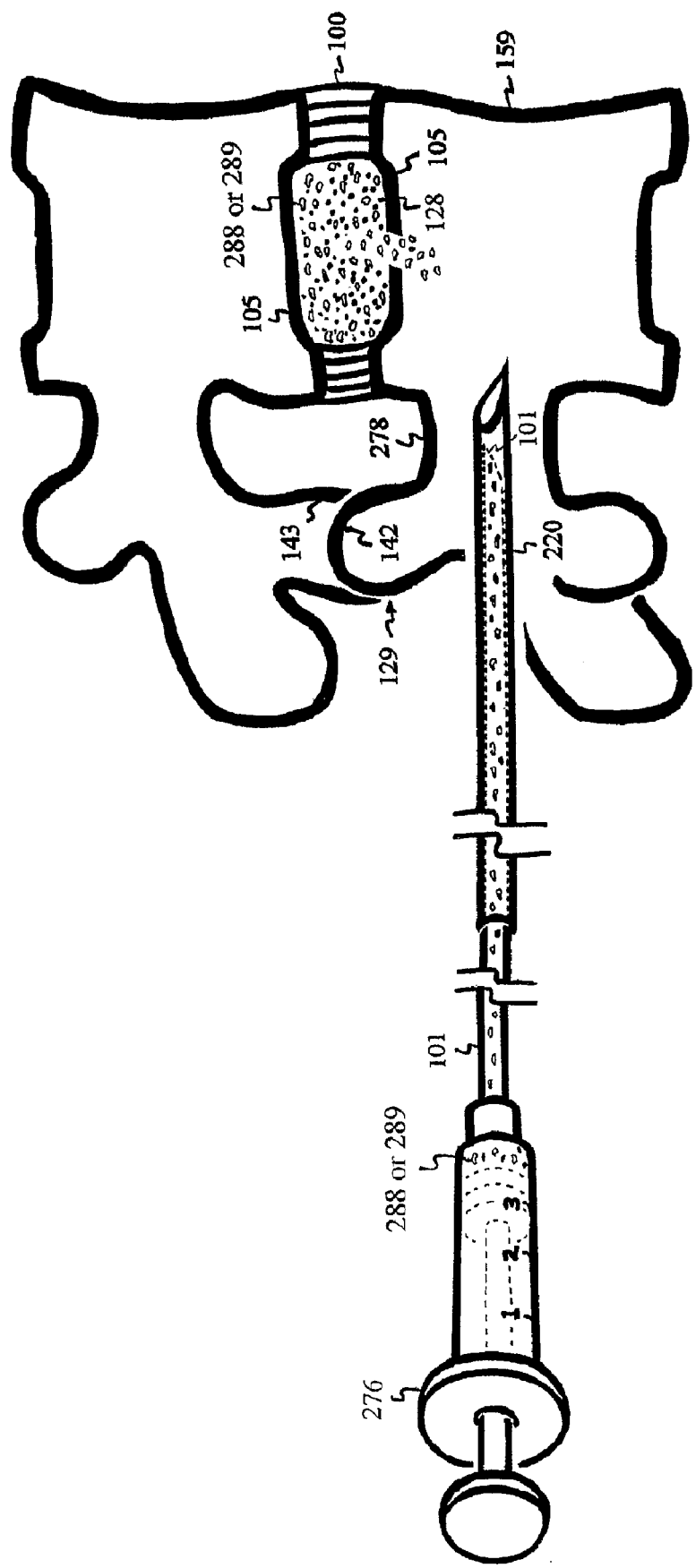
FIG. 10 depicts retrieval of the curved needle 101, resiliently straightened within the rigid needle 220.
Figure 11:
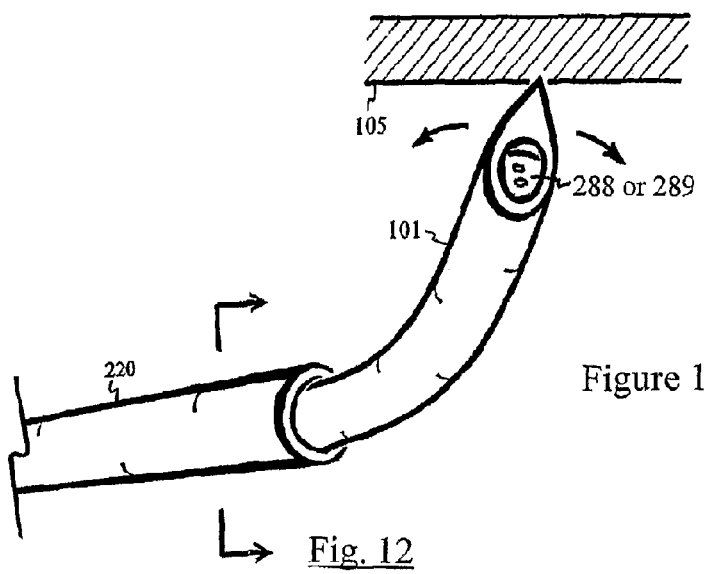
FIG. 11 depicts twisting of the curved needle 101 within the rigid sleeve 220 during endplate 105 puncturing. Twisting greatly hinders the capability of endplate 105 puncturing.
Figure 12:
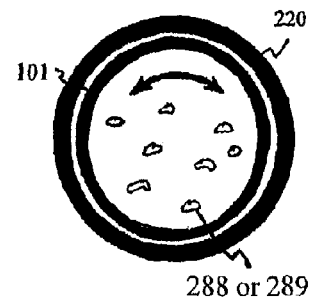
FIG. 12 shows the circular cross-sections of the curved needle 101 twisting within the rigid needle 220.

FIG. 6 shows insertion of the rigid needle 220 and elastically curved needle 101 into the pedicle 278 and partially into the vertebral body 159. The distal end of the rigid needle 220 is used to support the convex side of the deployed elastically curved needle 101 during calcified endplate 105 puncturing into the disc 100, as shown in FIG. 7. FIG. 8 shows a top view of the endplate 105 punctured by the supported elastically curved needle 101. Buffering agent 288 or filler 289 from syringe 276 is injected into the disc 100 through the elastically curved needle 100, as shown in FIG. 9. The curved needle 101 is then retrieved and resiliently straightened within the rigid needle 220, as shown in FIG. 10. The assembly of rigid needle 220, curved needle 101 and syringe 276 can be rotated 180° to puncture the inferior endplate 105 and inject buffering agent 288 or filler 289 into the inferior degenerated disc 100. Multiple factors prevent successful endplate puncture. For pedicle 278 entry and disc injection, the minimum length of the elastically curved needle 101 within the rigid needle 220 is about 10 cm, the proper length is about 15 cm. Since the curved needle 101 is elastic, it is likely to twist within the rigid needle 220, allowing directional shift at the tip of the needle 101 during contact with the calcified endplate 105. A lengthy curved needle 101 intensifies the twisting problem. The tip of the needle 101 is deflected by the endplate 105 and fails to puncture through the endplate 105, as shown in FIG. 11. A cross-sectional view of the curved needle 101 twisting within the rigid needle 220 is depicted in FIG. 12.

Figure 13:
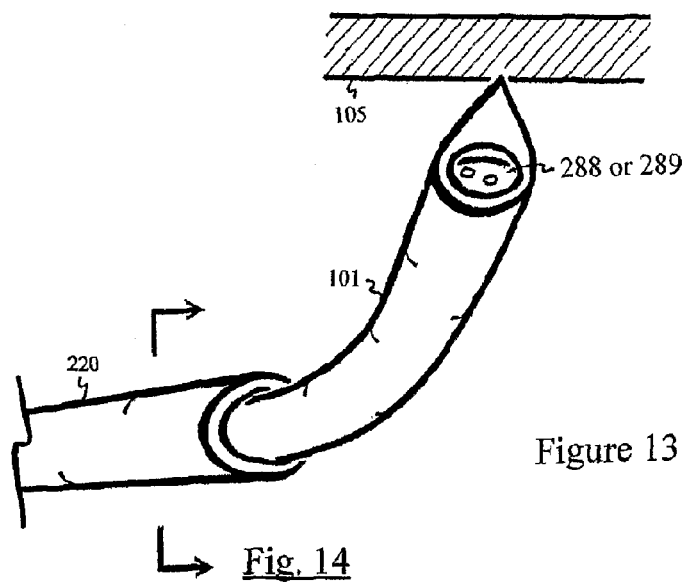
FIG. 13 depicts prevention of twisting during endplate 105 puncture by using elliptical cross-sections in curved needle 101 and sleeve 220.
Figure 14:
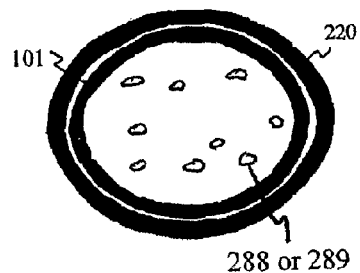
FIG. 14 shows the elliptical cross-sectional view of FIG. 13. Twisting or rotation of the elastic needle 101 within the rigid sleeve 220 is significantly limited.

To prevent twisting between the curved needle 101 and rigid needle/sleeve 220, the cross sections of both needles are made non-round. FIG. 13 shows elliptical cross-sections in both curved needle 101 and sleeve 220. An elliptical cross-sectional view of the curved needle 101 within the rigid needle 220 is depicted in FIG. 14 to ensure success of endplate 105 puncture.

Figure 15:
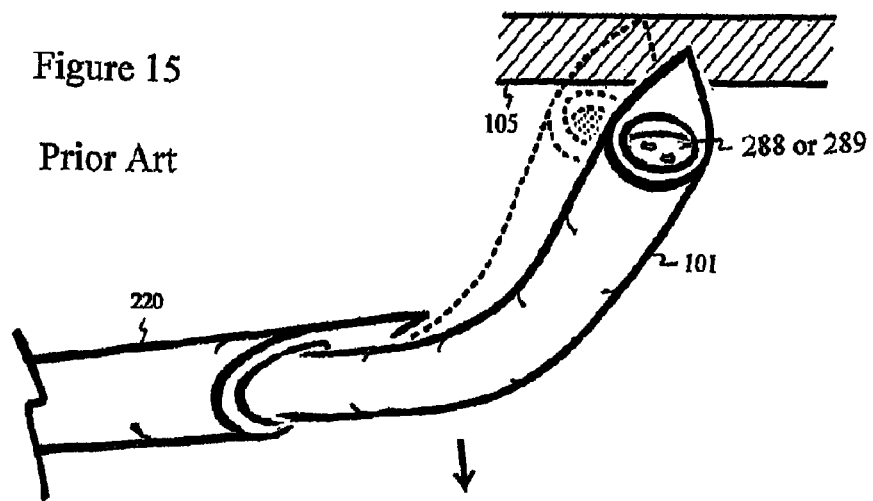
FIG. 15 depicts bending or drooping of the unsupported curved needle 101 during endplate 105 puncturing using prior art. Bending hinders endplate 105 puncturing.

Prior art, DE 44 40 346 A1 by Andres Melzer filed on Nov. 14, 1994 and FR 2 586 183-A1 by Olivier Troisier filed on Aug. 19, 1985, is not designed for puncturing hard surfaces, such as the calcified endplate 105. In prior art, distal tips of the rigid needles 220 are at the concave sides of their unsupported elastically curved needles 101, as shown in FIG. 15. During calcified endplate 105 puncture using the prior art, bending or drooping of the unsupported curved needle 101 is likely, resulting in failure to puncture the endplate 105.

Figure 16:
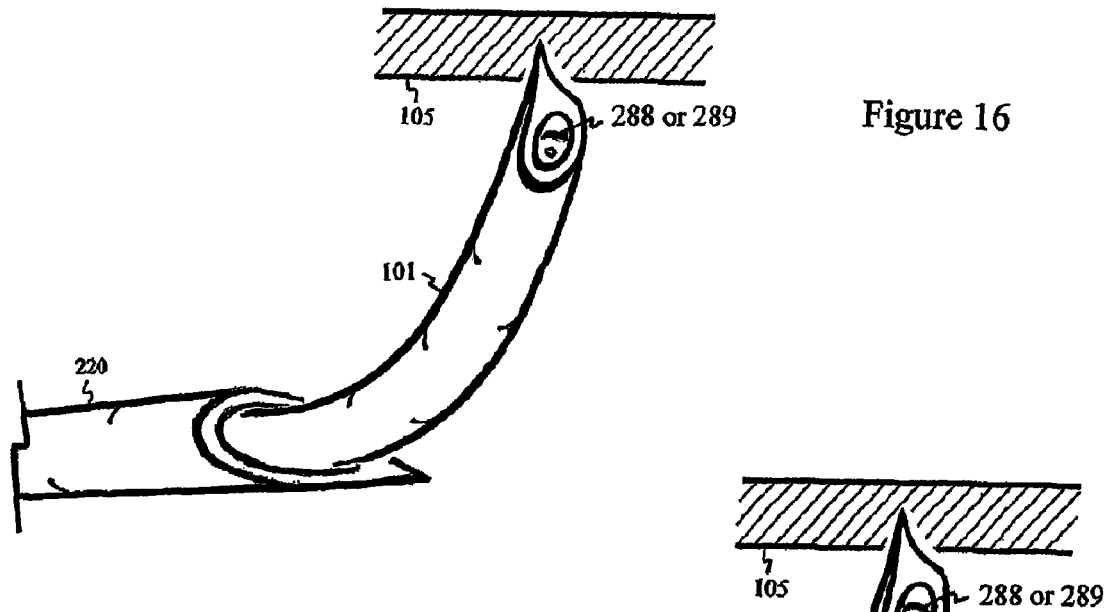
FIG. 16 shows support from the sharpened tip of the rigid needle 220 beneath the convex side of the curved needle 101 to reduce bending or drooping during endplate 105 puncturing.
Figure 17:
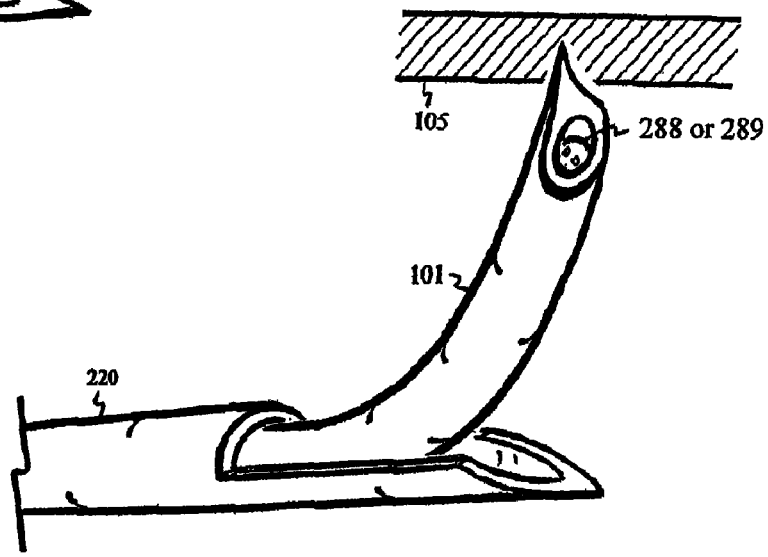
FIG. 17 depicts an extended distal end of the rigid needle 220 to lengthen the support beneath the convex side of the curved needle 101 during endplate 105 puncturing.
Figure 18:
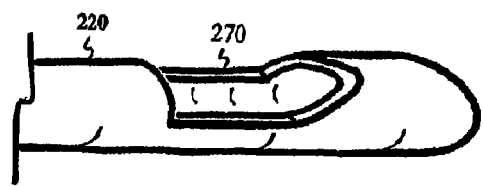
FIG. 18 shows a window 270 near the distal end of a sleeve 220 with an elliptical cross-section. The distal portion of the window 270 is slanted or sloped, conforming to the outer wall of the curved needle 101.
Figure 19:
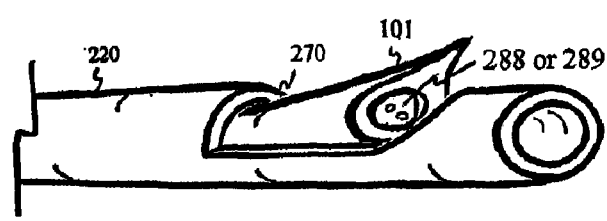
FIG. 19 depicts the sharp tip of the elastically curved needle 101 located on the concave side of the curvature for ease of protrusion through the window 270.
Figure 20:
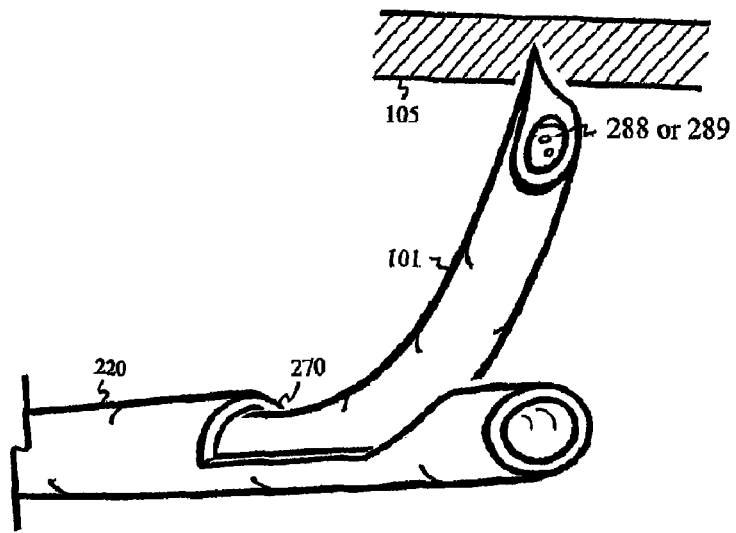
FIG. 20 shows support for the convex side of the curved needle 101 by the distal pocket of the window 270 securing the needle 101 to puncture the endplate 105.
Figure 21:
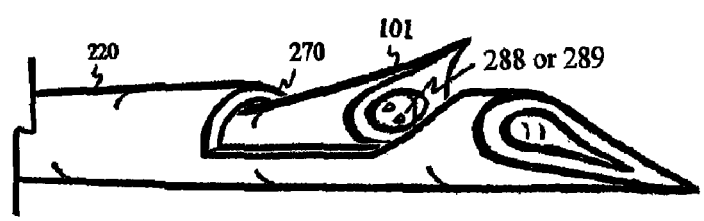
FIG. 21 shows a rigid needle 220 with the needle 101 at the securing window 270.

In this invention, the sharpened tip of the rigid needle 220 beneath the convex side of the curved needle 101 provides support to reduce bending or drooping during endplate 105 puncturing, as shown in FIG. 16. To further support the curved needle 101 for injection into the degenerated disc 100, an extended distal end of the rigid needle 220 lengthens the support beneath the convex side of the curved needle 101 during endplate 105 puncturing, as depicted in FIG. 17. A window 270 near the distal end of a rigid sleeve 220 with an elliptical cross-section is shown in FIG. 18. The distal portion of the window 270 is slanted or sloped, conforming to the outer wall of the curved needle 101. FIG. 19 shows the sharp tip of the elastically curved needle 101 located on the concave side of the curvature to avoid scraping or snagging on the distal portion of the window 270 during deployment of needle 101. The window 270 with the distal slanted configuration is made to saddle and secure the elastically curved needle 101 from deflecting during endplate 105 puncturing, as shown in FIG. 20. FIG. 21 shows a rigid needle 220 with securing or supporting window 270 for the elastically curved needle 101.

Figure 22:
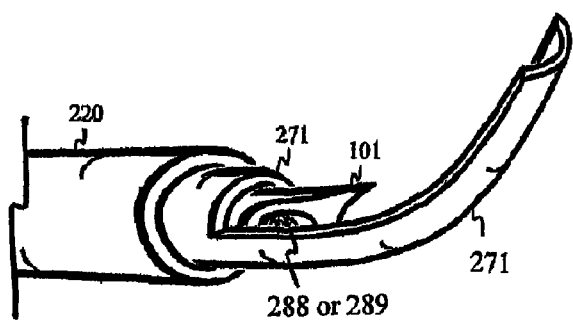
FIG. 22 depicts the elastically curved needle 101 within a curved shape memory extension 271. Both needle 101 and extension 271 are housed within a rigid sleeve 220.
Figure 23:
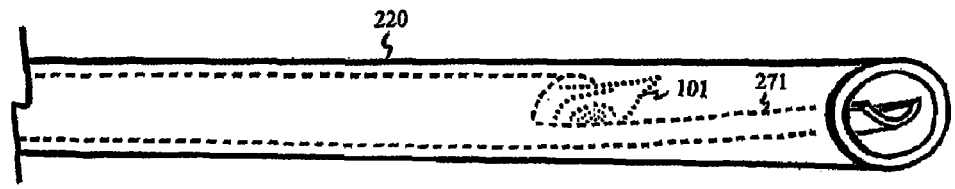
FIG. 23 shows resilient straightening of the shape memory extension 271 within the rigid sleeve 220.
Figure 24:
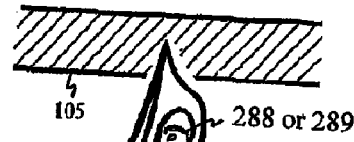
FIG. 24 shows the convex side support of the needle 101 by the extension 271 without increasing the size of the puncture at the endplate 105.
Figure 25:
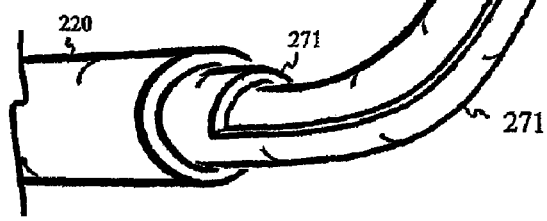
FIG. 25 shows a sharpened, tubular shape memory extension 271 to support endplate 105 puncturing.
Figure 25:
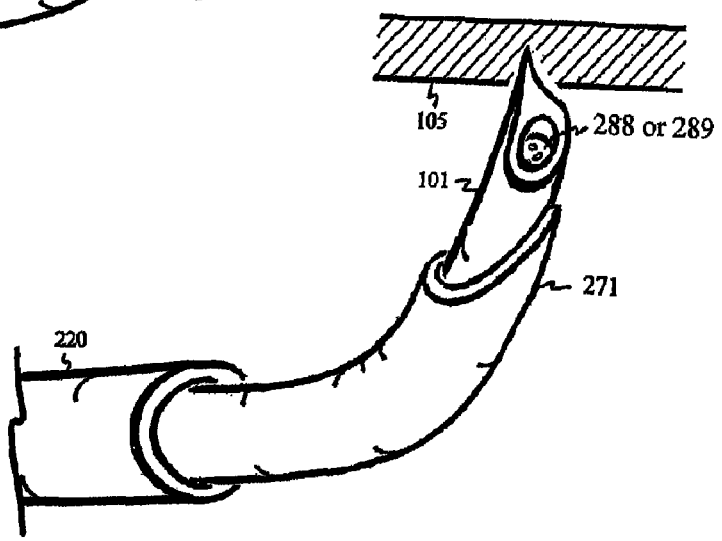

As back pain patients age, calcified endplates 105 harden further. Additional shape memory devices may be essential to support puncturing of the hardened calcified endplate 105 for injection into the degenerated disc 100. FIG. 22 depicts the elastically curved needle 101 housed within a curved shape memory extension 271 with a curved distal end. FIG. 23 shows resilient straightening of both the shape memory extension 271 and curved needle 101 within the rigid sleeve 220. FIG. 24 shows support at the convex side of the curved needle 101 by the extension 271, enabling needle 101 puncture into the calcified endplate 105. The curvature and inner wall of the curved shape memory extension 271 complement, support and shape-conform to the curvature and outer wall of the curved needle 101. Since the curved shape memory extension 271 supports only the base or convex side of the needle 101, the size of the punctured hole at the endplate 105 remains small to minimize loss of hydrostatic pressure or content of the disc 100. FIG. 25 shows a sharpened, tubular shape memory extension 271 for penetrating the cancellous bone within the vertebral body 159 and supporting endplate 105 puncturing.

Figure 26:
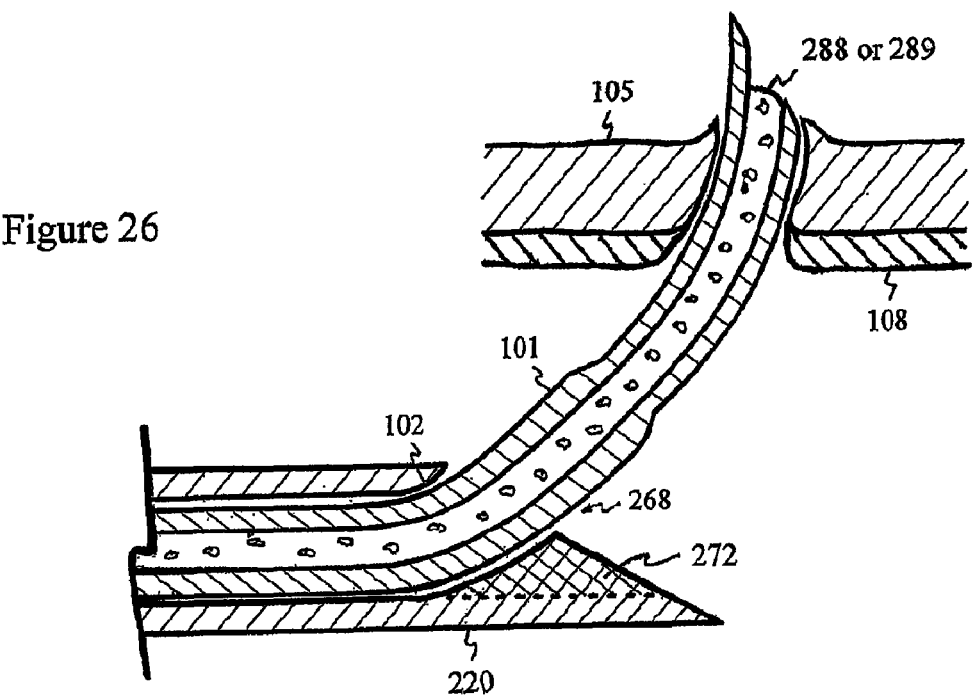
FIG. 26 shows a longitudinal cross section of a curved needle 101 with non-uniform outer diameter, supported by a ramp 272 within the lumen 268 of the rigid needle 220.

The elastically curved needle 101 can be made with non-uniform outer diameter, thinner at the distal end as shown in FIG. 26. The thin and sharp distal end of the curved needle 101 is used for puncturing a small opening at the calcified endplate 105. The thickened body of the curved needle 101 provides strength and support during endplate 105 puncture with crucial support at the base of the curvature near the rigid needle 220. The lumen 268 of the rigid needle 220 may have a bevel 102 and a double-sided ramp 272, as shown in FIG. 26. The bevel 102 at the distal end of the lumen 268 minimizes friction against the concave side of the curved needle 101 during deployment and retrieval. The double-sided ramp 272 is protruded at the side opposite to the bevel 102 with the distal side in continuation with the sharp tip or extended end of the rigid needle 220. The proximal side of the ramp 272 or protrusion can be shaped to conform to and support the convex side of the curved needle 101 during endplate 105 puncturing. The ramp 272 can be made with epoxy, solder or other hardened material, then shaped by machining. The ramp 272 can also be created during a molten process to seal the lumen 268 at the distal end. The sealed end is then cut, the ramp 272 and bevel 102 are shaped, and the lumen 268 is re-opened by machining.

Figure 27:
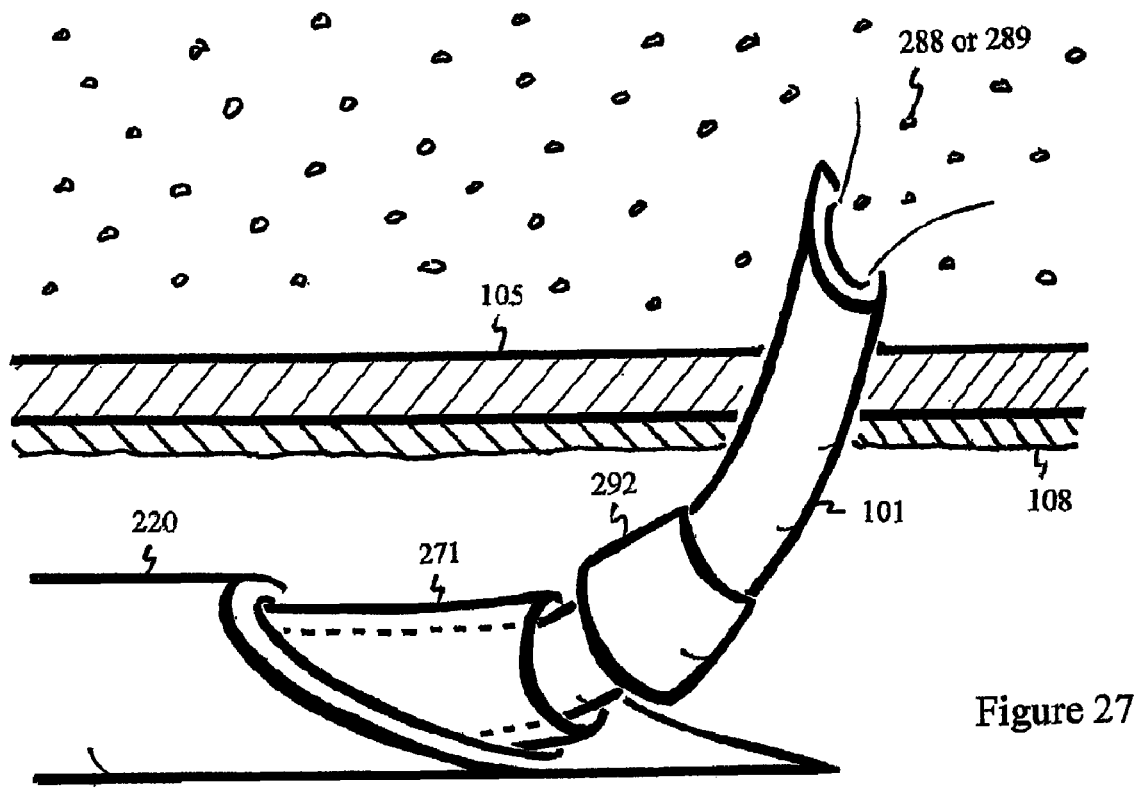
FIG. 27 shows an endplate plug 292, slidable over the curved needle 101, abutting a shape memory extension 271.
Figure 28:
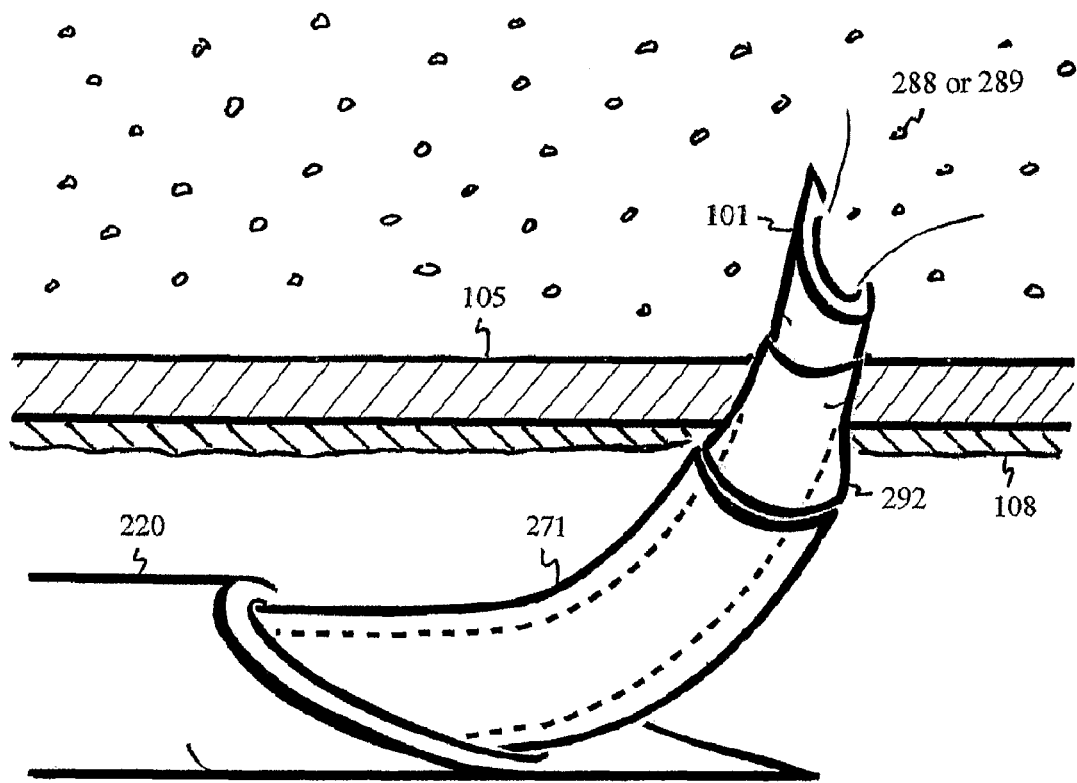
FIG. 28 shows advancement of the shape memory extension 271, pushing the endplate plug 292 to slide along the elastically curved needle 101 into the endplate 105 hole.
Figure 29:
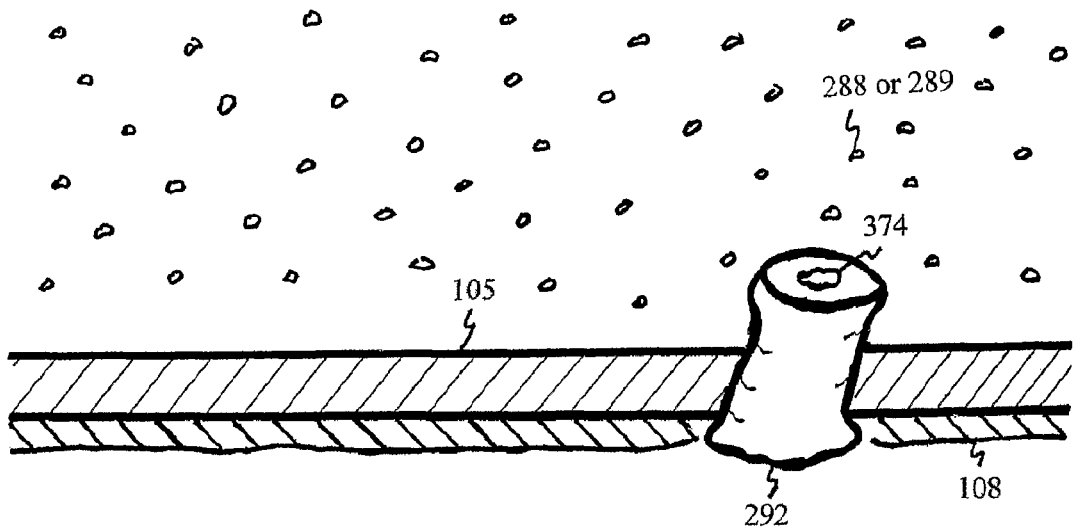
FIG. 29 shows swelling or sealing of the endplate plug 292 with collapsing lumen 374 occluding the puncture hole at the endplate 105.

After injecting buffering agent 288 or disc filler 289 from the syringe 276 into the degenerated disc 100, leakage into the vertebral body 159 is likely following needle 101 withdrawal. A shape conforming endplate plug 292 is positioned to slide over the curved needle 101, abutting a shape memory extension 271, as shown in FIG. 27. The plug 292 has a tapered outer wall, thin at the distal end and thick at the proximal end for sealing. After injection of buffering agent 288 or filler 289, the shape memory extension 271 is advanced to push the plug 292 into the puncture hole at the endplate 105, as shown in FIG. 28. While the curved needle 101 is slightly withdrawn from the endplate 105, the shape memory extension 271 is further advanced, pushing the plug 292 further into the endplate 105 and collapsing the inner lumen 374 of the soft or shape conforming plug 292, as shown in FIG. 29, to seal the buffering agent 288 or filler 289 within the degenerated disc 100. The plug 292 can be made with biocompatible material, such as collagen, hyaluronate, alginate, polyethylene glycol, polyurethane, silicon or other. The plug 292 can also swell from hydration to occlude the puncture hole at the endplate 105 and seal the lumen 374 of the plug 292.

Studies indicated that lumbar pain correlates well with high lactate levels and low pH. Antacid, buffering agent or base 288 can be injected from the syringe 276 through the curved needle 101 to neutralize the lactic acid within the degenerative disc 100, minimize acid irritation and alleviate back pain, as depicted in FIG. 9. The antacid, buffering agent or base 288 can be aluminum carbonate, aluminum hydroxide, aluminum oxide, aluminum phosphate, calcium carbonate, calcium hydroxide, calcium phosphate, hydrotalcite, magnesium carbonate, magnesium glycinate, magnesium hydroxide, magnesium oxide, magnesium trisilicate, sodium bicarbonate, sodium carbonate, sodium phosphate or other.

Sulfate is an essential ingredient for biosynthesizing the sulfated glycosaminoglycans, responsible for retaining water within the intervertebral disc 100. Transport of sulfate into the disc 100 is hindered by the acidic pH. After injection of antacid 288, the normalized pH enhances transport of sodium sulfate into the disc 100 to promote biosynthesis of sulfated glycosaminoglycans necessary for retaining additional water, capable of sustaining compressive loads upon the disc 100. As a result, excessive loading and strain on the facet joints 129 are minimized and pain is alleviated. In addition, collagen within the annulus 378 of the disc 100 is sensitive to acid hydrolysis. Acidic pH accelerates decomposition and hydrolysis of the degenerating disc 100. Injection of antacid 288 normalizes pH to preserve peptide bonds in collagen and proteoglycans in disc 100.

Back pain from spinal instability initiated by disc 100 degeneration is very common. Similar to repairing and re-inflating a flat tire of a car, filling and fortifying the degenerated disc 100 minimize instability, lift compressive loads from the facet joints 129 and alleviate back pain. Through minimally invasive punctures using a rigid needle 220 through the pedicle 278 and curved needle 101 through the calcified endplate 105, disc filler 289 is infused from the syringe 276 to fortify and support the degenerated disc 100.

Figure 54:
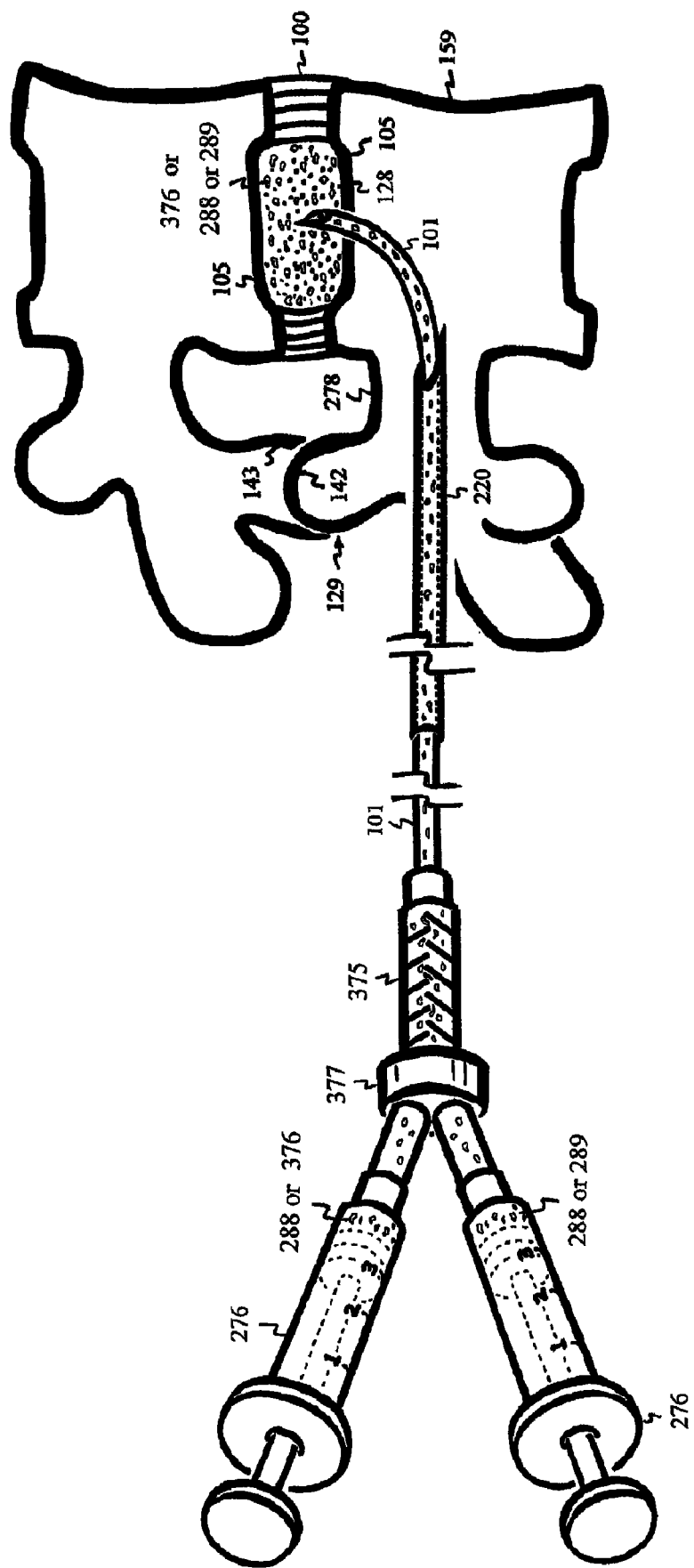
FIG. 54 shows two syringes 276 connected to a static mixer 375 for mixing and injecting substances through the curved needle 101 into the degenerated disc 100.

Methacrylic acid or methyl-methacrylic acid, with molecular structure shown in FIG. 30, is a monomer, which can be polymerized into bone cement, poly-methyl-methacrylate (PMMA) as shown in FIG. 31. Methacrylic acid, methyl-methacrylic acid can be used as disc fillers 289 to repair, inflate and stabilize degenerated disc 100 with the polymerized PMMA. Polymerization of methyl-methacrylic acids into PMMA is promoted by a base or radical generator. Two syringes 276 connect to the proximal end of a static mixer 375, the distal end of the mixer 375 connects to the elastically curved needle 101, as shown in FIG. 54. Methyl-methacrylic acid as a filler 289 is filled in one syringe 276, while the base or radical generator is filled as the second filler 376 in another syringe 276. The filler 289 and second filler 376 are injected simultaneously into the static mixer 375, infusing the polymerizing methyl-methacrylic acids into the degenerated disc 100. As a result, the viscosity of both fillers 289 and 376 increases, preventing leakage through herniated disc 100 or the endplate 105 punctured hole.

Polyethylene glycol (PEG) in FIG. 32 can be a biocompatible filler 289, capable of retaining water as the sulfated glycosaminoglycans in the nucleus pulposus 128. Methoxy PEG in FIG. 33, methoxy PEG amine in FIG. 34, di-amine PEG in FIG. 35, methoxy sulfhydro PEG in FIG. 36, and di-sulfhydro PEG in FIG. 37 can be used as fillers 289 and crosslinking derivatives of PEG. The PEG can also be activated for crosslinking reactions with N-hydroxysuccinimide, maleimide, thioester, acrylate and vinyl sulfone with molecular structure of methoxy-PEG-N-hydroxysuccinimide in FIG. 38, PEG-propionate-N-hydroxysuccinimide in FIG. 39, PEG-butanoate-N-hydroxysuccinimide in FIG. 40, PEG-succinimidyl-N-hydroxysuccinimide in FIG. 41, methoxy-PEG-maleimide in FIG. 42, PEG-thioester in FIG. 43, maleimide-PEG-N-hydroxysuccinimide in FIG. 44, maleimide-PEG-maleimide in FIG. 45, methoxy-PEG-di-maleimide in FIG. 46, acrylate-PEG-N-hydroxysuccinimide in FIG. 47 and vinyl sulfone-PEG-N-hydroxysuccinimide in FIG. 48.

Figure 49:
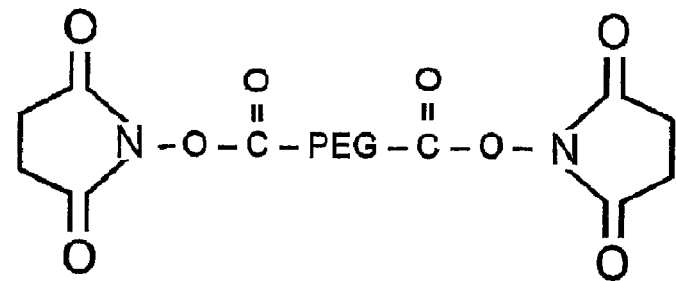
FIG. 49 shows a crosslinking reaction between di-NHS-PEG and di-sulfhydro-PEG, fillers 289 within the static mixer 375 and within the disc 100.
Figure 49:
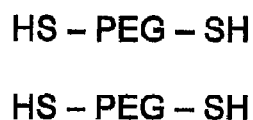
Figure 49:
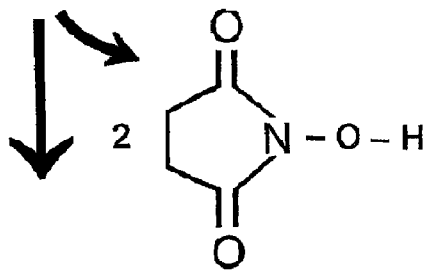
Figure 49:
Figure 49:

Di-N-hydroxysuccinimide-PEG as a filler 289 is loaded in a syringe 276, and di-sulfhydro-PEG as the second filler 376 in pH 5.5-8.0 solution is loaded in another syringe 276. Both fillers 289 and 376 are mixed within the static mixer 375 and injected through the curved needle 101 into the degenerated disc 100. The chemical reaction is shown in FIG. 49. The rate of crosslinking reaction is pH sensitive, where high pH promotes rapid crosslinking to prevent leakage from herniated disc 100 or the punctured hole at the endplate 105. As a result, the spinal segment is stabilized and the heavy load on facet joint 129 is partially lifted to alleviate back pain.

Figure 50:
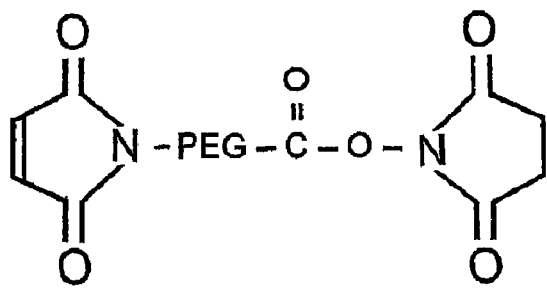
FIG. 50 shows a crosslinking reaction between MAL-PEG-NHS and di-sulfhydro-PEG, fillers 289.
Figure 50:
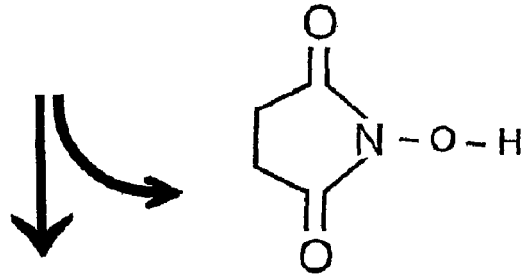
Figure 50:
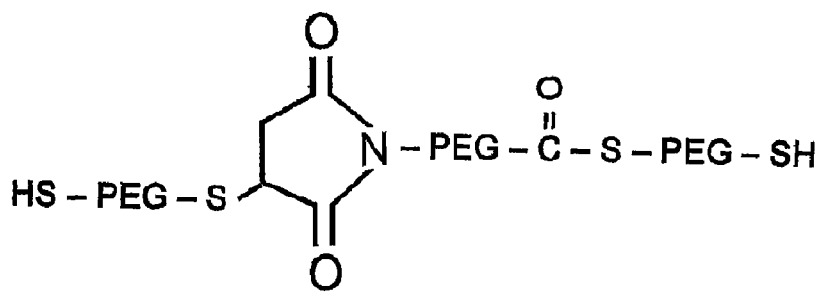

Similarly, maleimide-PEG-N-hydroxysuccinimide can be a filler 289 in a syringe 276, while di-sulfhydro-PEG can be the second filler 376 for mixing into a polymerizing PEG to fortify the degenerated disc 100 from within, through the minimally invasive needle puncturing procedure. The chemical reaction is shown in FIG. 50.

Figure 51:
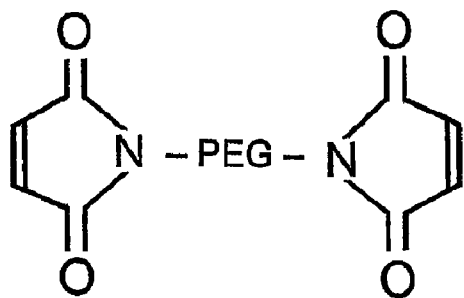
FIG. 51 shows a crosslinking reaction between di-MAL-PEG and di-sulfhydro-PEG, fillers 289.
Figure 51:
Figure 51:
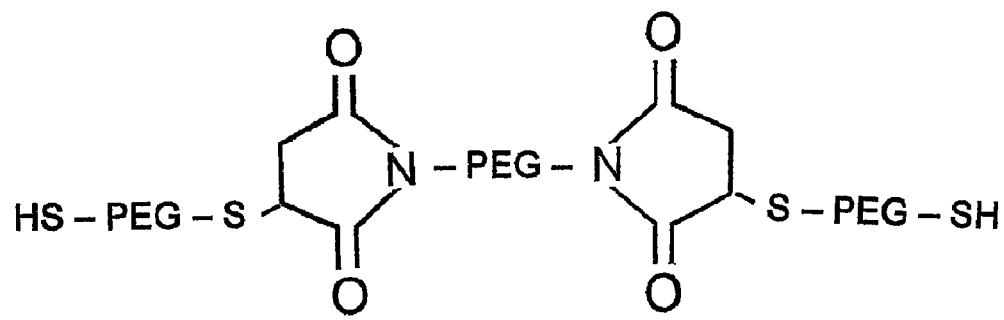
Figure 51:
Figure 52:
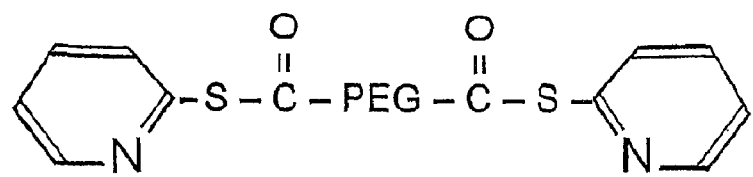
FIG. 52 shows a crosslinking reaction between di-thioester-PEG, di-amine-PEG and di-sulfhydro-PEG, fillers 289.
Figure 52:
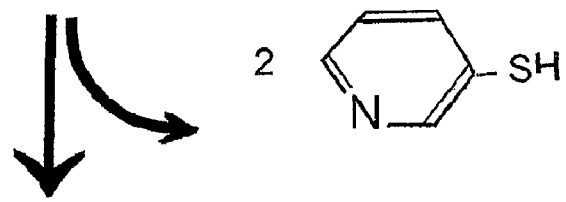
Figure 52:
Figure 52:
Figure 53:
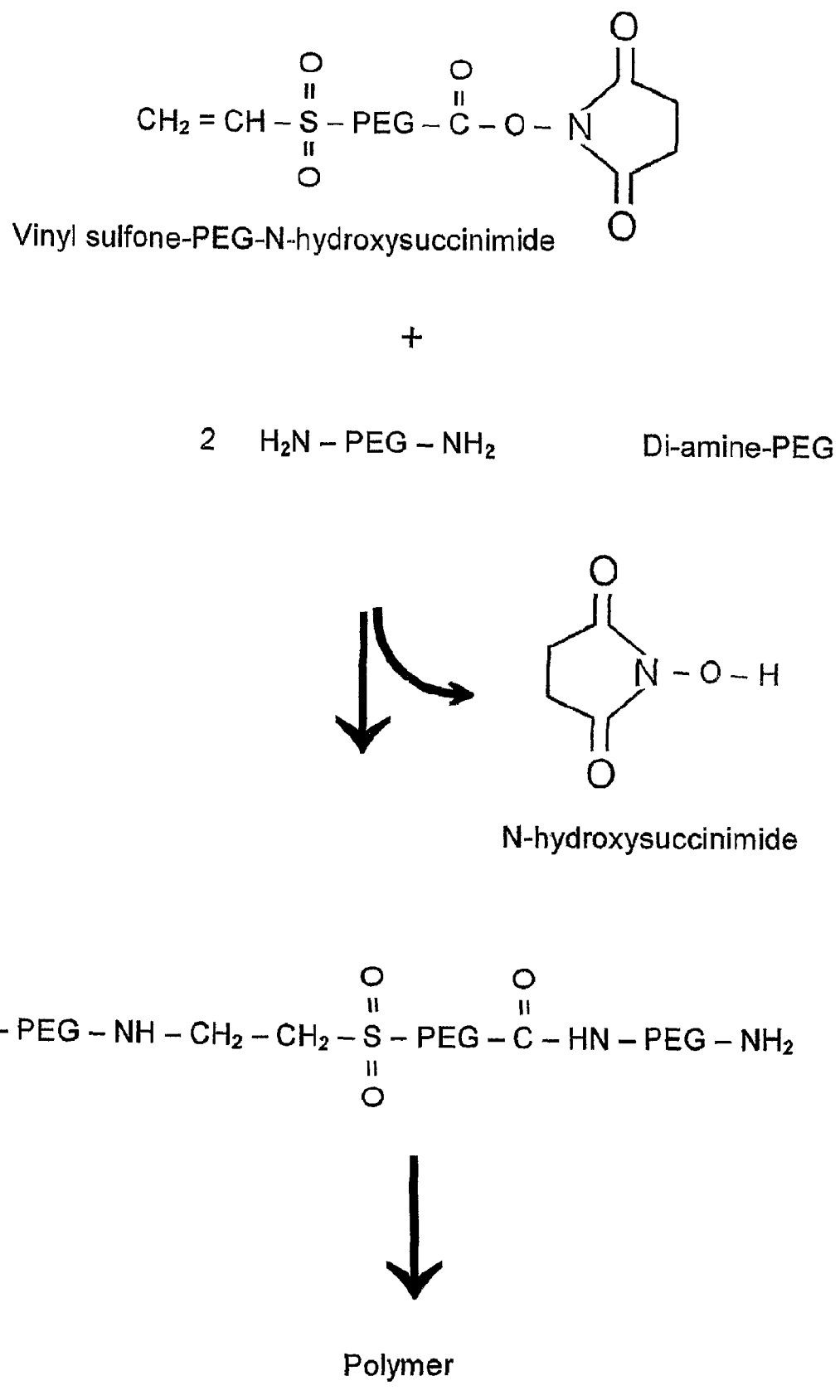
FIG. 53 shows a crosslinking reaction between vinyl sulfone-PEG-NHS and di-amine-PEG, fillers 289.

Di-maleimide-PEG and di-sulfhydro-PEG can be another filler 289 and the second filler 376 with chemical reaction shown in FIG. 51. Di-sulfhydro-PEG is usually more biocompatible than di-amine-PEG. However, the disc 100 is avascular with little immuno exposure. As a disc filler 289 or 376, the di-sulfhydro-PEG can probably be interchangeable with di-amine-PEG. The chemical reaction of di-thioester-PEG with di-amine-PEG and di-sulfhydro-PEG is shown in FIG. 52. Vinyl-sulfone-PEG as one of the function groups can be used to crosslink with di-amine-PEG as shown in FIG. 53 to form PEG polymeric filler 289 within the degenerated disc 100 to stabilize the painful segmental instability. Other filler 289, such as polyurethane, collagen, hyaluronate, silanolate or calcium/barium crosslinked alginate, can also be used.

Since nutrient permeability through the calcified endplate 105 diminishes with age, injection of nutrients 288 can significantly increase biosynthesis of chondroitin sulfate and keratan sulfate to retain additional water and regain swelling pressure of the degenerative disc 100. Unlike the traditional needle used in prior art (Klein R G, Eek B C, O'Neill C W, Elin C., Mooney V., Derby R R: Biochemical injection treatment for discogenic low back pain: a pilot study, Spine J., May-June 3(3), 220-226, 2003), the elastically curved needle 101 can inject nutrients into the centers of L4-5, L5-S1 problematic discs even though they are shielded between the ilia. Nutrients in the syringe 276 through the curved needle 101 can be chondroitin sulfate, keratan sulfate, glucose, glucuronate, galactose, glucosamine, N-acetyl-6-sulfate-D-galactosamine, N-acetyl-6-sulfate-D-glucosamine, proline, glycine, amino acids, thiamine, riboflavin, niacin, niacinamide, pantothenate, pyridoxine, cyanocobalamin, biotin, folate, ascorbate, alpha-tocopheryl, magnesium, selenium, copper, manganese, chromium, molybdenum, vanadium, zinc, silicon, silicone, silicic acid, silanolate, silane, boron, boric acid, sodium sulfate or other. By injecting nutrients, production of sulfated glycosaminoglycans may significantly increase to restore swelling pressure. Restoration of swelling pressure within the nucleus pulposus 128 reinstates the tensile stresses within the collagen fibers of the annulus 378, thus reducing the inner bulging and shear stresses between the layers of annulus 378. Similar to a re-inflated tire, disc 100 bulging is reduced and nerve impingement is minimized. The load on the facet joints 129 is also reduced to ease pain, the motion segment is stabilized, and disc 100 space narrowing may cease. The progression of spinal stenosis is halted and/or reversed to ease pain.

A growth factor can also be injected through the elastically curved needle 101, puncturing through the calcified endplate 105 into the disc 100 to promote disc regeneration. Injection of the growth factor, antacid 288, filler 289 or nutrients through the pedicle 278 using the well supported elastically curved needle 101 minimizes risks and optimizes success of endplate puncture.

The rigid needle 101 can be made with stainless steel or other metal or alloy. The elastically curved needle 101 and shape memory extension 271 can be formed with nickel-titanium alloy. The needle 101, rigid needle 220 and shape memory extension 271 can be coated with lubricant, tissue sealant, analgesic, antibiotic, radiopaque, magnetic and/or echogenic agents.

It is to be understood that the present invention is by no means limited to the particular constructions disclosed herein and/or shown in the drawings, but also includes any other modification, changes or equivalents within the scope of the claims. Many features have been listed with particular configurations, curvatures, options, and embodiments. Any one or more of the features described may be added to or combined with any of the other embodiments or other standard devices to create alternate combinations and embodiments. The elastically curved needle 101 can be called the elastic needle 101 or the resilient needle 101. Some figures show the rigid needle 220 being blunt as a rigid tube 220. The rigid needle 220 or needle 101 can be generally described in the claims as a sheath with a lumen. Injection of the antacid 288 can also be done with a straight or traditional needle, especially for L3-4 level and above. The vertebral body 159 can be called a vertebra.

It should be clear to one skilled in the art that the current embodiments, materials, constructions, methods, tissues or incision sites are not the only uses for which the invention may be used. Different materials, constructions, methods, coating or designs for the injection device can be substituted and used. Nothing in the preceding description should be taken to limit the scope of the present invention. The full scope of the invention is to be determined by the appended claims.

What is claimed is:

1. A method for increasing pH within an intervertebral disc, the method comprising the steps of:
    (a) filling an antacid in a syringe connecting to a needle;
    (b) inserting said needle into an intervertebral disc;
    (c) injecting said antacid through said needle into the intervertebral disc to neutralize lactic acid produced within the intervertebral disc, and to increase pH of the intervertebral disc, thereby alleviating back pain;
    (d) removing said needle and syringe from the intervertebral disc.

2. The method for increasing pH within an intervertebral disc of claim 1, wherein a beveled tip of said needle is used to puncture the intervertebral disc.

3. The method for increasing pH within an intervertebral disc of claim 1, wherein said antacid is chosen from the group of antacids consisting of: aluminum carbonate, aluminum hydroxide, aluminum oxide, aluminum phosphate, calcium carbonate, calcium hydroxide, calcium phosphate, hydrotalcite, magnesium carbonate, magnesium glycinate, magnesium hydroxide, magnesium oxide, magnesium trisilicate, sodium bicarbonate, sodium carbonate and sodium phosphate.

4. The method for increasing pH within an intervertebral disc of claim 1, wherein said needle in step (a) has a coating.

5. The method for increasing pH within an intervertebral disc of claim 4, wherein said coating is chosen from the group of coatings consisting of: lubricant, tissue sealant, analgesic, antibiotic, radiopaque, magnetic and echogenic coating.

6. The method for increasing pH within an intervertebral disc of claim 1, wherein in step (c) said antacid is injected by actuating a plunger in said syringe.

7. The method for increasing pH within an intervertebral disc of claim 1, wherein in step (b) said needle is inserted through a pedicle of a vertebral body.

8. The method for increasing pH within an intervertebral disc of claim 1, wherein in step (b) said needle through an endplate into the intervertebral disc.

9. The method for increasing pH within an intervertebral disc of claim 1, wherein in step (a) said antacid is a buffering agent.

10. The method for increasing pH within an intervertebral disc of claim 1, further comprising a step (e) moving a distal portion of said the needle out from a distal end of a sheath surrounding said needle, thereby allowing said needle to resume a curved configuration.

11. The method for increasing pH within an intervertebral disc of claim 1, wherein in step (b) said needle is curved.

12. The method for increasing pH within an intervertebral disc of claim 1, wherein in step (b) said needle is straight.

13. The method for increasing pH within an intervertebral disc of claim 1, wherein the intervertebral disc is a lumbar disc, and wherein in step (b) said needle is a resiliently curved needle that enters posterior-laterally into the lumbar disc.

14. The method of claim 1, further comprising a step (e) injecting a growth factor.

15. The method of claim 1, further comprising a step (e) actuating the injection device to inject a second and a third substance into the intervertebral disc.

16. The method of claim 15, further comprising a step (f) mixing said second substance and said third substance within a static mixer before injecting into the intervertebral disc.

17. The method of claim 16, wherein in step (f) mixing and injecting include depressing two plungers within two syringes.

* * * * *